(12) United States Patent
Yoshida et al.

(10) Patent No.: US 6,900,888 B2
(45) Date of Patent: *May 31, 2005

(54) METHOD AND APPARATUS FOR INSPECTING A PATTERN FORMED ON A SUBSTRATE

(75) Inventors: Minoru Yoshida, Yokohama (JP); Shunji Maeda, Yokohama (JP); Atsushi Shimoda, Hiratsuka (JP); Kaoru Sakai, Yokohama (JP); Takafumi Okabe, Yokohama (JP); Masahiro Watanabe, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/650,756

(22) Filed: Aug. 29, 2003

(65) Prior Publication Data

US 2004/0124363 A1 Jul. 1, 2004

Related U.S. Application Data

(63) Continuation-in-part of application No. 10/218,463, filed on Aug. 15, 2002.

(30) Foreign Application Priority Data

Sep. 13, 2001 (JP) .......................................... 2001-277681
Sep. 13, 2002 (JP) .......................................... 2002-267554

(51) Int. Cl.[7] .............................................. G01N 21/88
(52) U.S. Cl. ................................. 356/237.4; 356/237.5; 250/559.42; 250/559.4
(58) Field of Search ................. 356/237.1, 237.2–237.5, 356/239.1–239.8, 630–632; 250/559.4–559.48

(56) References Cited

U.S. PATENT DOCUMENTS

| | | | | |
|---|---|---|---|---|
| 5,774,222 A | * | 6/1998 | Maeda et al. | 356/394 |
| 6,031,607 A | * | 2/2000 | Miyazaki | 356/237.1 |
| 6,084,716 A | * | 7/2000 | Sanada et al. | 359/629 |
| 6,288,780 B1 | * | 9/2001 | Fairley et al. | 356/237.1 |
| 6,369,888 B1 | * | 4/2002 | Karpol et al. | 356/237.5 |
| 6,621,571 B1 | * | 9/2003 | Maeda et al. | 356/237.5 |

FOREIGN PATENT DOCUMENTS

| | | | |
|---|---|---|---|
| JP | 59-226317 | * | 12/1984 |
| JP | 62-231924 | * | 10/1987 |
| JP | 07-318326 | * | 12/1995 |
| JP | 08-320294 | * | 12/1996 |
| JP | 10-78668 | * | 3/1998 |

* cited by examiner

*Primary Examiner*—Richard A. Rosenberger
*Assistant Examiner*—Vincent P. Barth
(74) *Attorney, Agent, or Firm*—Antonelli, Terry, Stout & Kraus, LLP

(57) ABSTRACT

The inventive method and apparatus for detecting defects of a microscopic circuit pattern by imaging the pattern at high resolution comprises an objective lens for imaging the subject pattern, a laser illumination means for illuminating the pupil of the objective lens, means of diminishing the coherency of the laser illumination, an accumulative detector, and means of processing the signal detected by the detector. The method and apparatus are capable of imaging the subject pattern at high sensitivity and high speed based on the illumination by a short wavelength, which is indispensable for the enhancement of resolution, particularly based on a laser light source which is advantageous for practicing, with a resulting image being the same or better in quality as compared with an image resulting from the ordinary discharge tube illumination, whereby it is possible to detect microscopic defects at high sensitivity.

23 Claims, 23 Drawing Sheets

FIG. 8A
FIG. 8B
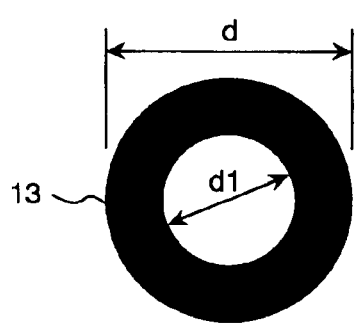
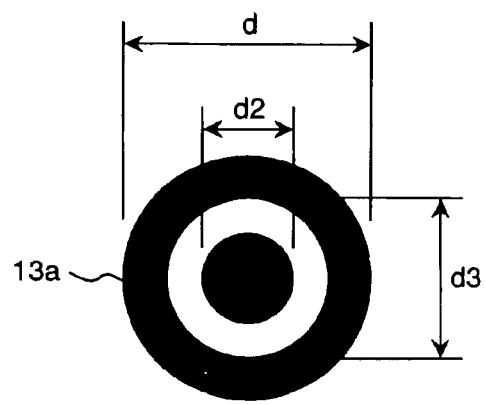
FIG. 9A
FIG. 9B
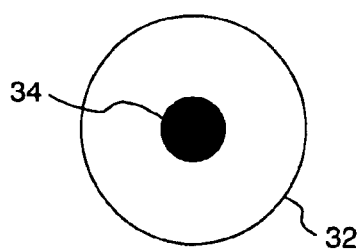
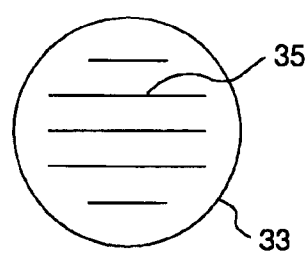

METHOD AND APPARATUS FOR INSPECTING A PATTERN FORMED ON A SUBSTRATE

CROSS REFERENCE TO RELATED APPLICATION

This application is a continuation-in-part of U.S. application Ser. No. 10/218,463, filed Aug. 15, 2002, the subject matter of which is incorporated by reference herein.

BACKGROUND OF THE INVENTION

The present invention relates to the inspection of pattern for detecting defects (short-circuits, line breakages, etc.) and foreign particle on a pattern under test, and particularly to a method and apparatus of pattern inspection for detecting defects and foreign particle on a pattern of semiconductor wafer, liquid crystal display panel, photomask, etc. In the following explanation, the term "defect" is used to signify also foreign particle inclusively.

There is a conventional pattern defect inspection apparatus which is designed to image a pattern under test with an imaging device such as a line sensor, while moving the pattern, and compare the image signal in terms of tone levels with the image signal which has been delayed by a prescribed time length, thereby recognizing the inequality to be the presence of a defect, as described in Japanese Patent Laid-Open No. H7 (1995)-318326.

There is known a conventional technique pertinent to the pattern defect inspection, as disclosed in Japanese Patent Laid-Open No. H8(1996)-320294. The technique of this patent publication deals with the high-accuracy inspection of microscopic defects of a pattern formed on a semiconductor wafer or the like where each chip includes high pattern density areas such as memory mats and low pattern density areas such as peripheral circuits. Specifically, the pattern is imaged and a resulting image signal is D/A converted, and a resulting digital image signal is rendered the gradating conversion such that the high pattern density areas and low pattern density areas have a certain relation in terms of brightness or contrast based on the frequency distribution of brightness of the image signal. The image signal resulting from gradating conversion is compared with a comparative image signal resulting from gradating variation in a state of position matching thereby to detect accurately a microscopic defect.

There is known a conventional technique for inspecting a pattern of photo-mask, as disclosed in Japanese Patent Laid-Open No. H10(1998)-78668. The technique of this patent publication uses a light source of UV laser such as excimer laser, with the coherency of laser being diminished by a revolving diffusion plate which is placed to cut in the light path, to illuminate the photo-mask uniformly thereby to image the pattern, and calculates the characteristic value from a resulting image data to assess the quality of photo-mask.

There are excimer laser exposure apparatus as disclosed, for example, in Japanese Patent Laid-Open Nos. S59(1984)-226317 and Sho. 62(1987)-231924.

In the recent LSI manufacturing, circuit patterns formed on wafers have their width decreased to become 0.25 μm or less to meet the demand of high-density integration, and this dimension is the limit of resolution of the imagery optical system. Therefore, the application of high NA based design of imagery optical system and super-high resolution technique are in progress.

However, the high NA based design is already at a physical limit, and the breakthrough approach is to shorten the wavelength of imaging light into the ranges of UV (ultraviolet) wavelengths of 300–380 nm, DUV (deep ultraviolet) wavelengths of 190–300 nm, VUV (vacuum ultraviolet) wavelengths of 100–190 nm, and EUV (extreme ultraviolet) wavelengths of the order of 10 nm.

Due to the requirement of high-speed inspection, the scheme of subject scanning with a spot-focused laser beam cannot be adopted. Illumination of subject with a wide full-field laser light creates speckles, which cause overshooting and undershooting called "wringing" at edge of circuit pattern, resulting in a degraded image quality.

SUMMARY OF THE INVENTION

The present invention provides a method and apparatus for the inspection of a microscopic circuit pattern to detect defects based on the high speed and high resolution imaging of the circuit pattern. The present invention also provides a manufacturing method of microstructured semiconductor devices based on the use of the above-mentioned pattern inspection method and apparatus.

The inventive method and apparatus use a light source of UV light or UV laser, with a means of alleviating the creation of speckles of UV light or UV laser being provided on the light path, to illuminate the subject surface by the UV light of diminished coherency, thereby imaging the subject. The UV light (the ultraviolet light) is assumed to include the DUV light.

Means of alleviating the creation of speckles caused by the UV light according to this invention is a diffusion plate, and there is provided a means of moving the plate relative to the light beam in the direction virtually normal to the optical axis. In addition, with the intention of improving the contrast of pattern, it is devised, based on the fact that the polarization state of laser light can be manipulated, to be able to detect partially-polarized light components by controlling the direction of polarization of illumination light and the elliptic factor.

The inventive pattern inspection apparatus for defect detection is designed to include a light source which emits the UV light (the ultraviolet light), laser or UV laser, a light quantity adjusting means which adjusts the quantity of the UV light, laser or UV laser emitted by the light source, an illumination range defining means which defines the illumination range of the UV light, laser or UV laser put out from the light quantity adjusting means, an irradiation means which diminishes the coherency of the UV light, laser or UV laser put out from the illumination range defining means and casts onto a subject, an imaging means which images the subject irradiated by the irradiation means to produce an image signal, and a defect detecting means which detects a defect of a pattern, which is formed on the subject, based on information carried by the image signal of subject produced by the imaging means.

The inventive pattern inspection method for defect detection is designed to include the steps of diminishing the coherency of the laser light emitted by a laser light source, casting a resulting laser light onto the surface of a subject, with a pattern being formed thereon, through an objective lens while varying the irradiation direction with time, imaging the subject irradiated by the laser light, and comparing the image signal resulting from the imaging of the subject with a reference image signal which has been stored in advance thereby to detect a defect of the pattern.

The inventive method of inspecting a pattern formed on a subject for detecting a defect is designed to include the steps of casting a UV laser light, with the coherency thereof being diminished, onto the surface of the subject, imaging the subject surface irradiated by the UV laser light to produce an image signal, processing the image signal to detect a defect of 100 nm or less on the subject, and releasing information on the positions of the detected defect of 100 nm or less on the subject.

It is also possible obviously to use a DUV light source, VUV light source or EUV light source having wavelengths of 400–50 nm besides the UV light source or UV laser light source.

These and other objects, features and advantages of the present invention will become apparent from the following more particular description of preferred embodiments of the invention, as illustrated in the accompanying drawings.

BRIEF DESCRIPTION OF THE DRAWINGS

FIGS. 8A and 8B are plan views of the limiting aperture based on this invention;

FIG. 9A is a plan view showing the state of discharge tube illumination on the pupil of imaging objective lens, and FIG. 9B is a plan view showing the state of discharge tube illumination in the view field;

DESCRIPTION OF THE PREFERRED EMBODIMENTS

The method and apparatus for pattern defect inspection based on embodiments of this invention will be explained with reference to the drawings.

Figure 1:
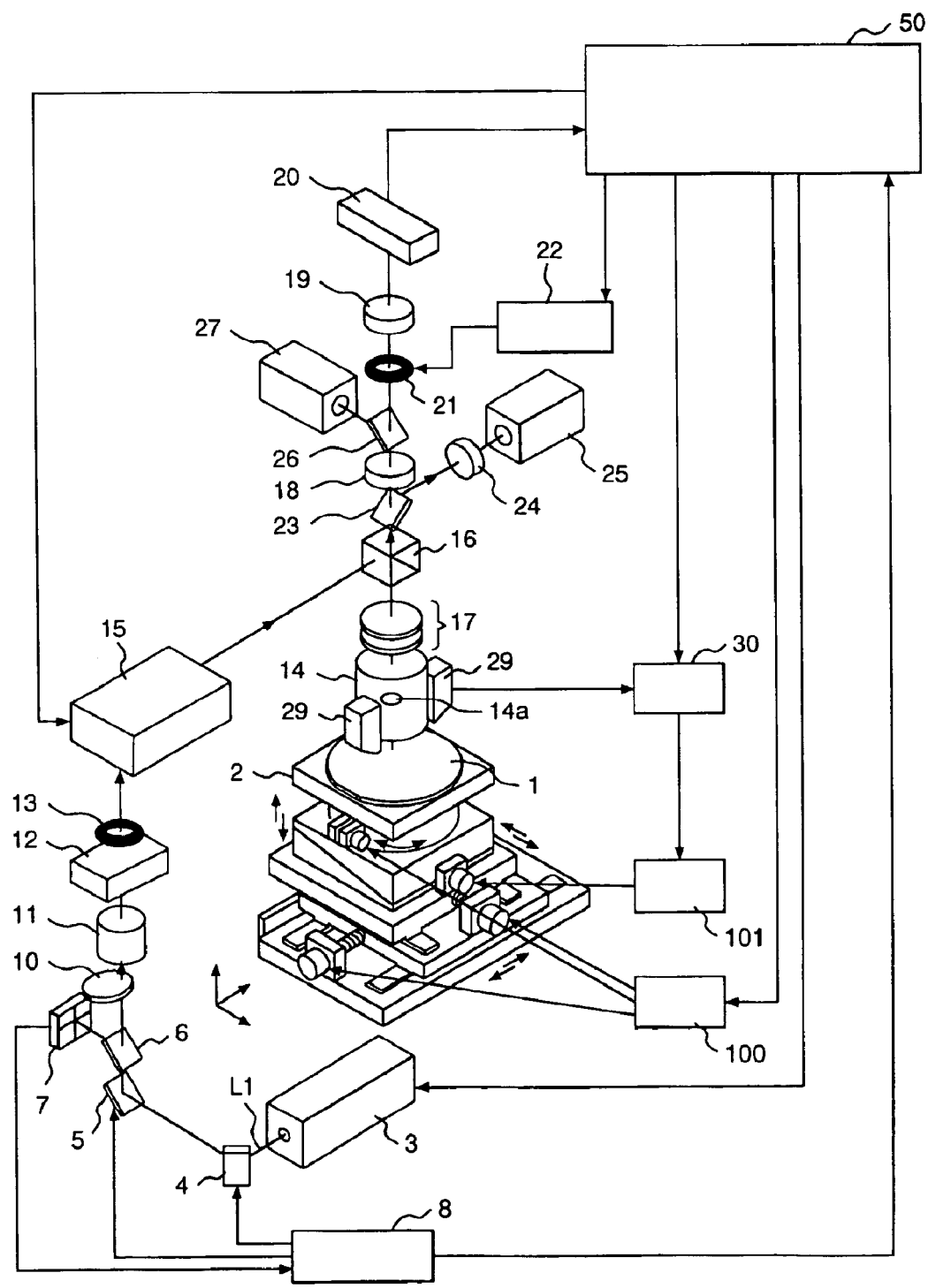
FIG. 1 is a perspective diagram showing in brief the structure of a pattern defect inspection apparatus based on an embodiment of this invention.

FIG. 1 shows an apparatus based on an embodiment of this invention. The apparatus includes a stage 2, which is made up of X, Y, Z and θ (rotation) stages, on which a semiconductor wafer (subject) 1 having a pattern to be inspected is placed. The X, Y and θ stages are operated by a drive circuit 100. The Z stage is operated by another drive circuit 101. An illumination light source 3 which illuminates the subject 1 consists of a UV laser source having a wavelength of 266 nm or 355 nm for example. The UV laser source is a device which implements the wavelength conversion for the solid YAG laser with nonlinear optical crystal, etc. to produce the third harmonic (355 nm) or fourth harmonic (266 nm) of the fundamental wave. A laser light source having a wavelength of 193 nm or 248 nm may be used alternatively. Using a laser source having a wavelength of 193 nm or shorter, if available, will enhance the resolution of imaging. The laser oscillation mode can be either continuous oscillation or pulsative oscillation. The continuous oscillation mode is preferable in consideration of imaging of the subject 1 while moving the stage continuously.

The illumination light source 3 emits a light beam L1, which is reflected by a mirror 4 for setting an intended optical axis, reflected by another mirror 5, and conducted through an ND filter 10 so that the quantity of light is limited to the light level necessary for the inspection. The mirrors 4 and 5 are moved by a drive circuit 8 to adjust the light beam in the up/down and right/left directions in a certain manner (not shown).

The ND filter 10 and the mirror 5 are interposed by a partial mirror 6. The partial mirror 6 having a reflectivity of small percentage transmits most part of the light. The reflected light beam from the partial mirror 6 is cast onto a divisional sensor 7. The sensor 7 having four divisions in this embodiment measures the balance of light levels of all divisions in a certain manner (not shown), and puts the difference values into the drive circuit 8. For example, the divisional sensor 7 has its individual light quantities balanced when the optical axis of the illumination light beam is at the center of sensor. In this case, the mirrors 4 and 5 do not activate. If the optical axis of the illumination light source 3 varies by some reason, the divisional sensor 7 goes out of balance in light quantity. This variation of light quantity of the divisional sensor 7 indicates a positional error, causing the mirrors 4 and 5 to be operated by the drive circuit 8 on a feedback basis so that the divisional sensor 7 is kept balanced in light quantity. The total light quantity of the divisional sensor 7 indicates the output of the illumination light source 3, and accordingly it can be utilized to monitor the fall of output of the illumination light source 3. The drive circuit 8 implements the calculation for the sensor output, and a controller (not shown) controls the illumination light source 3 to keep a constant light output.

The light beam emitted by the illumination light source 3 has a diameter of around 1 mm in general, which is too small to be used as illumination light, and therefore the light beam is expanded by a beam expander 11. An illumination light path switching optical system 12 is intended to define the illumination range on the subject 1. An limiting aperture 13, which is located at the position conjugate with the pupil 14a of an objective lens 14, is intended to limit the NA which is incident to the pupil 14a.

The expanded light beam is directed to a coherency diminishing optical system 15 which is intended to diminish the coherency of the laser beam emitted by the illumination light source 3. The coherency diminishing optical system 15 can be any optical system which lower the coherency of laser in a time-wise or space-wise fashion.

The coherency diminishing optical system 15 releases a light beam, which is directed by a beam splitter 16 to the objective lens 14. The beam splitter 16, which can be a polarization beam splitter, is designed to reflect the illumination light from the illumination light source 3 thereby to render the bright field illumination for example to the subject 1 through the objective lens 14. The beam splitter 16, if it is a polarization beam splitter, functions to reflect or transmit the laser beam when it has a polarization direction parallel or perpendicular, respectively, to the reflection plane. Since a laser beam is a polarized light beam inherently, the polarization beam splitter 16 is capable of totally reflecting the laser beam. A set of polarizing devices 17 function to control the polarization direction of the laser illumination light and reflected light to adjust the polarization ratio of the illumination light arbitrarily so that the reflected light is not uneven in brightness at the destination due to the shape and difference of density of the pattern, and it consists of a halfwave plate and quarterwave plate for example.

The reflected light from the subject 1 goes back through the objective lens 14 and conducted through the polarizing devices 17 and beam splitter 16.

The reflected light is focused by imagery lenses 18 and 19 on an image sensor 20. A diaphragm 21 is located at the position conjugate with the pupil 14a of the objective lens 14. The diaphragm 21 which is operated by a drive circuit 22 is capable of squeezing the light beam in a certain manner (not shown). The maximum opening of diaphragm is to allow the pupil 14a of the objective lens 14 to do full transmission, and it is adjusted appropriately.

A movable mirror 23 can be placed between the beam splitter 16 and the lens 18, in which case an image of the subject 1 can be formed in a camera 25 by a lens 24.

A movable mirror 26 can be placed between the diaphragm 21 and the imagery lens 18, in which case an image of the subject 1 can be formed in a camera 27 by the lens 18.

The camera 25 is used for the wide-field overall observation of the subject 1, i.e., at low magnification, while the camera 27 is used for the narrow-field observation of the subject 1, i.e., at high magnification and high resolution.

The image sensor 20 has a pixel size of 0.05–0.3 µm in terms of dimension on the subject depending on the combination of the imagery lenses 18 and 19, and it is designed to produce a tonal image signal in response to the brightness (tone) of the reflected light from the pattern to be inspected on the subject 1 (e.g., semiconductor wafer). The tonal image signal is put in to an image signal processing circuit 50, which implements the image processing to detect defects of the pattern.

The objective lens 14 has its focal depth decreasing with the decrease of wavelength, and therefore it is necessary to position (adjust) the surface of the subject 1 always at the focal point of the objective lens 14. The objective lens 14 has its property of resolution affected by various kinds of aberration, and it can have the best performance by the optimal selection of the material of the lens 14 and the coating of the lens surface depending on the wavelength used. On this account, it is becoming difficult for the apparatus of this structure to implement the focusing operation by use of the objective lens 14. Therefore, it is advantageous to implement the off-line focusing operation without using the objective lens 14. In this embodiment, a focal point detecting system 29 is disposed adjacently to the objective lens 14. The height of subject 1 from the periphery of objective lens 14 is measured by a certain manner (not shown), and a feedback control circuit 30 operates on a drive circuit 101 to move the subject 1 toward the focal point. The focal point detecting system 29 is positioned to match with the focal point of objective lens 14 in advance.

These optical systems are set up on an optical rack to organize the illumination light source, illumination optical system, imaging optical system, and optical sensor. The optical rack is installed in a certain manner (not shown) on a firm table, for example, where the stage 2 is set up, and this setup environment enables the stable inspection against disturbances including the temperature variation and vibration.

Figure 2:
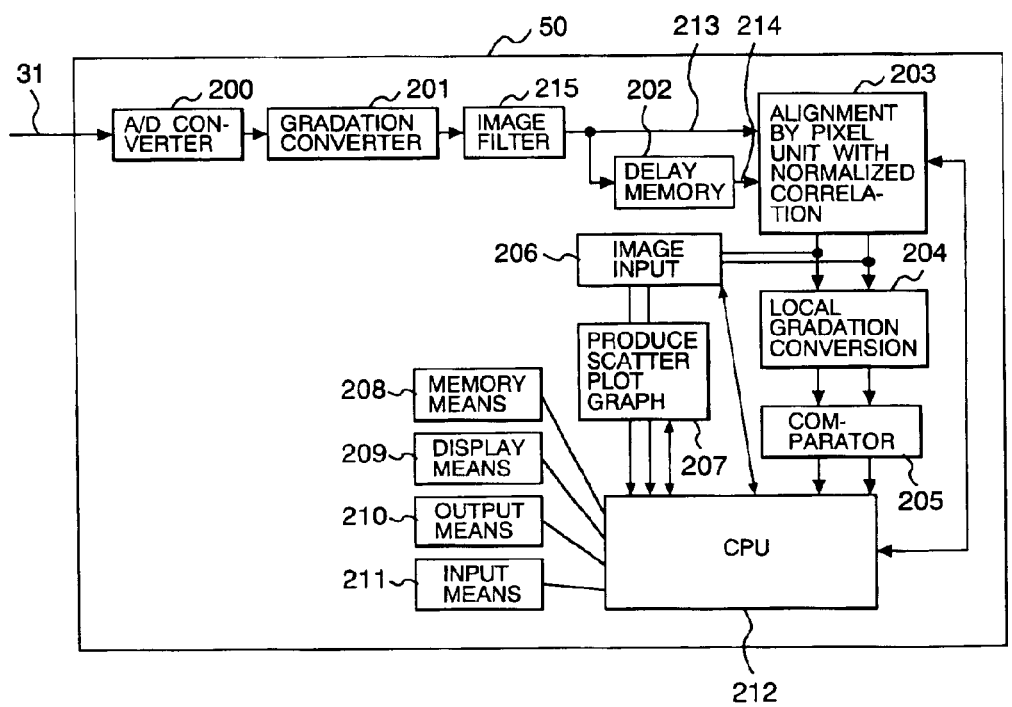
FIG. 2 is a block diagram showing in brief the arrangement of the image processor of the pattern inspection apparatus based on this invention.

FIG. 2 shows the image signal processing circuit 50. The circuit 50 includes an A/D converter 200, gradation converter 201, image filter 215, delay memory 202, image alignment portion 203, local gradation converter 204, comparator 205, CPU 212, image entry 206, scatter plot graph generator 207, memory means 208, display means 209, output means 210, and input means 211. The A/D converter 200 of 10 bits for example converts the tonal image signal 31 produced by the image sensor 20 into a digital image signal and releases an image signal of the subject. The gradation converter 201 renders the gradation conversion as described in Japanese Patent Laid-Open No. H8 (1996)-320294 to the 10-bit image signal released by the A/D converter 200.

The gradation converter 201 performs the logarithmic conversion, exponential conversion, or polynomial conversion thereby to modify (compensate) the image, and releases an 8-bit digital signal for example. The image filter 215 removes efficiently noises, which are specific to images formed by the UV light, from the image which has been rendered the gradation conversion and modification. The delay memory 202 for storing reference image signals delays and stores the output image signals released by the image filter 215 for one or more cells or one or more chips formed on the semiconductor wafer. One cell is the unit of pattern repetition within a chip. The image filter 215 may be located at the output of the delay memory 202 alternatively.

The alignment portion 203 evaluates the positional deviation of the image signal (image signal detected from the subject) 213 which has been rendered the gradation conversion by the gradation converter 201 from delayed image signals (reference image signals) 214 read out of the delay memory 202 based on the normalized correlation, thereby implementing positional alignment by pixel unit between the image signals 213, 214.

The local gradation converter 204 renders the gradation conversion to one or both image signals so that the characteristic values (brightness, differentiation value, standard deviation, texture, etc.) of both signals become equal when a defect does not be existed.

The comparator 205 compares the image signals resulting from gradation conversion by the gradation converter 204 to detect the defect based on the difference of characteristic values. Specifically, the comparator 205 compares the detected image signal with the reference image signal which has been delayed in proportion to the cell pitch by the delay memory 202. The CPU 212 produces defect inspection data based on layout coordinate data of the semiconductor wafer 1, which has been entered through the input means 211 such as a keyboard or disk storage, and stores the produced data in the memory means 208. The defect inspection data can be displayed on the display means 209 such as a display screen, and also can be put in to the output means 210.

The comparator 205, which can be the one described in detail in Japanese Patent Laid-Open No. S61 (1986)-212708, is made up of an image alignment circuit, differential image detecting circuit which detects the difference of the position-aligned images, inequality detecting circuit which binary-digitizes the differential image, and characteristics detecting circuit which calculates the area, length (projection length), coordinates, etc. from the binary output. The image entry 206 enters the images, which have been rendered the positional alignment of the images with pixel unit by the image alignment portion 203, in synchronous or asynchronous manner for producing a scatter plot graph of the images. The scatter plot graph generator 207 produces a scatter plot graph between the characteristic values in terms of each category of the produced image and reference image entered by the image entry 206, and displays a resulting figure on the display means 209 for example.

Figure 3:
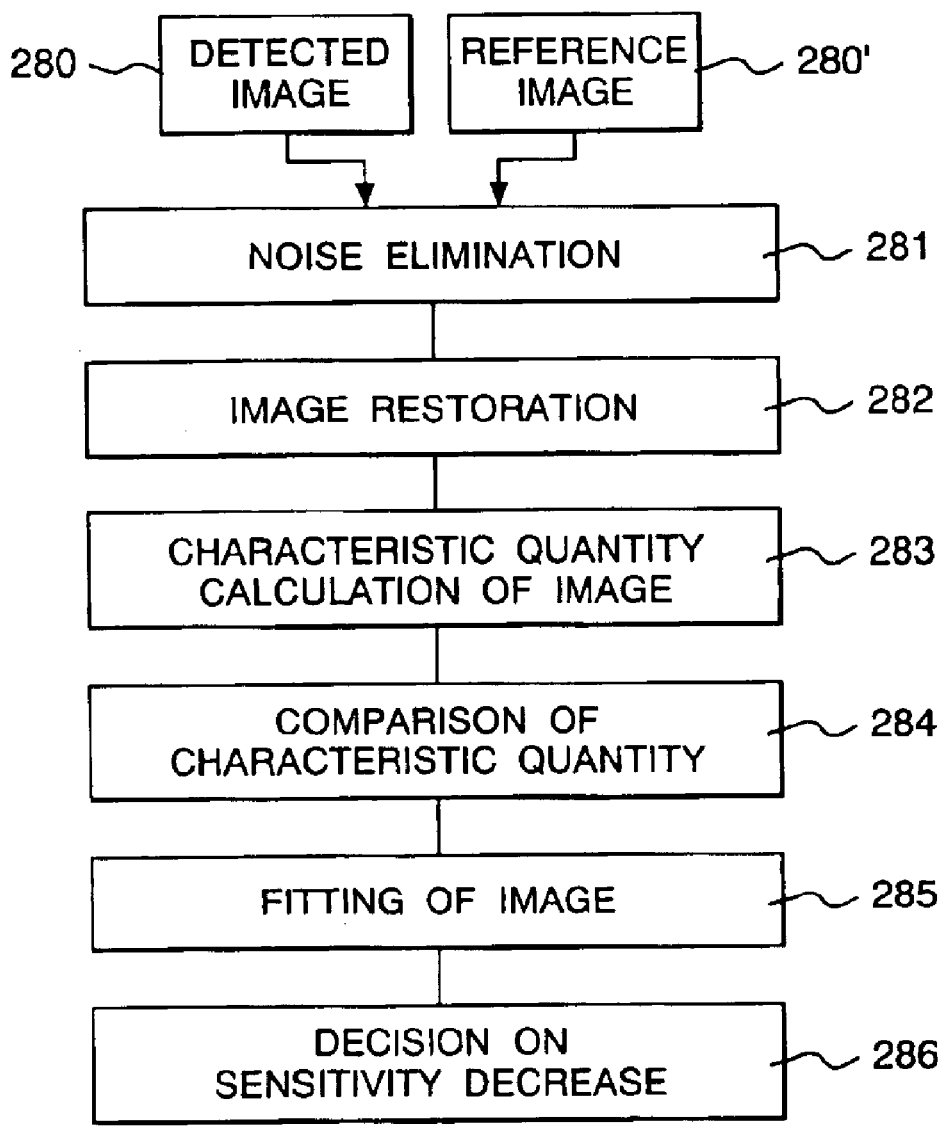
FIG. 3 is a flowchart showing the sequential process of the image filter based on this invention.
Figure 4:
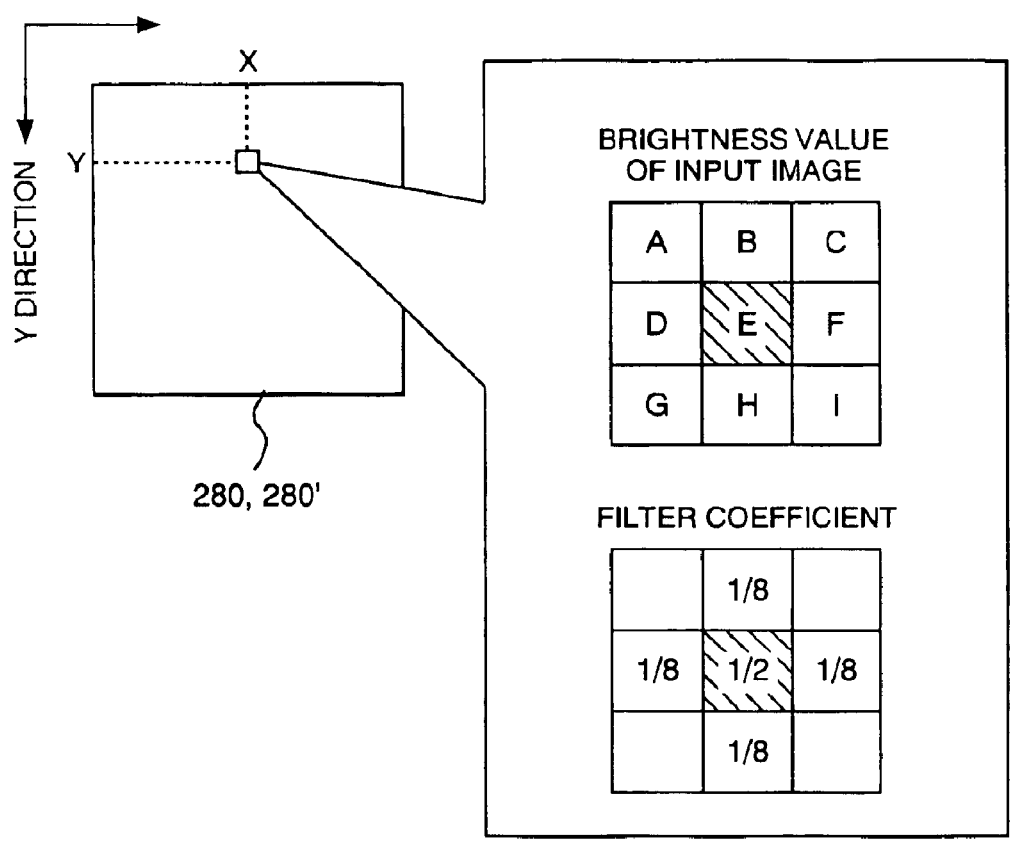
FIG. 4 is a plan view of an image, explaining the image filter for image processing based on this invention.

An example of the image filter 215 will be explained with reference to FIG. 3 showing the sequential process. Initially, the input images 280 and 280' undergo the noise elimination 281 to improve the image quality and enhance the s/n property. Various kinds of filters can be used selectively for noise elimination depending on the subject of inspection and the nature of noise. One example is to apply a weight to the neighboring pixel values. Specifically, a weighting factor is multiplied to the values of neighboring pixels of n×m around the pixel of one's observation and the results are summed. FIG. 4 shows an example, in which a weighting factor of ⅛ is applied to the n=3 by m=3 neighboring pixel values. The pixel of one's observation (i,j) has its value F(i,j) expressed by formula (1).

$$F(i,j) = B \cdot 1/8 + D \cdot 1/8 + F \cdot 1/8 + H \cdot 1/8 + E \cdot 1/2$$

The size and factor of the filter can be varied flexibly by use of a lookup table.

Another example is a median filter. This scheme is to take the center value of luminance values within the predetermined area, and it can eliminate the influence of singular points. Still another example is to use a Gaussian function. This scheme smoothes the image by convoluting a 2-dimensional Gaussian function (formula (2)) having a mean value of 0 and variance of $\sigma^2$ for the image f(x,y) based on formula (3).

$$G(x,y) = (1/2\pi\sigma^2) \cdot \exp(-(x^2+y^2)/2\sigma^2) \quad (2)$$

$$F(x, y) = G(x, y) \otimes f(x, y) \quad (3)$$
$$= \int\int G(x+u, y+v) \cdot f(x, y) du dv$$

where the $\otimes$ represents convolution.

Still another example available is to use the Fourier transform to remove noises which arise regularly.

The subsequent step is the restoration 282 of the image which has been deteriorated in quality by the noise removal. One example of restoration is to use a Wiener filter. This filtering results such an image that the mean square error of the restored image f'(x, y) from the input image f(x, y) is minimal.

Next, it is examined as to whether the produced image and reference image to be compared differ significantly in appearance. Assessment indexes include the contrast, disparity of brightness (standard deviation), and noise frequency. If the images have a large difference in characteristic quantities, the images undergo the characteristic quantity calculation 283 so that the difference of characteristic quantities is narrowed. This process can be based on the use of Wiener filter between the produced image and the reference image. Following the comparison of characteristic quantities 284 and fitting of images 285, decision of sensitivity decrease 286 is implemented. In case the fitting of characteristic quantities is infeasible in the detection process, the comparator is lowered in sensitivity so as to suppress the false generation.

The defect calculation by the image processor 24 can be accomplished based on the scheme described in detail in Japanese Patent Laid-Open No.2001-194323.

Figure 5A:
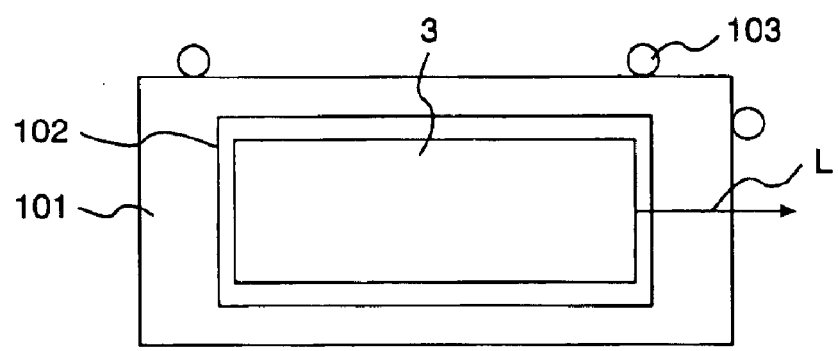
FIG. 5A is a front view of the illumination light source, showing the manner of attachment of the laser light source based on this invention.
Figure 5B:
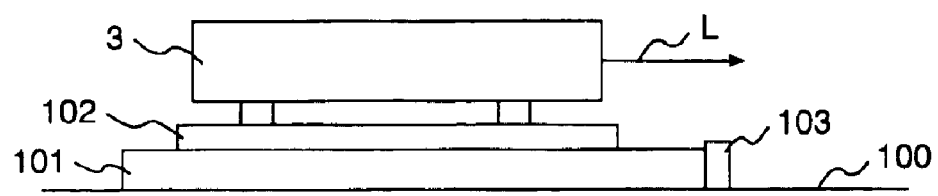
FIG. 5B is a plan view of the light source.

Next, the illumination light source 3 will be explained. A light source of the shorter wavelength is required to attain the higher resolution of imaging, and the laser is conceived to be advantageous significantly as a light source to perform high-luminance illumination in the UV wavelength range which is most effective for the enhancement of resolution. Accordingly, the inventive method and apparatus adopt the laser-based illumination. FIGS. 5A and 5B show by plan view and side view, respectively, the structure of an illumination light source. The illumination light source 3 is fixed on a plate 102. Another plate 101 is positioned and fixed on an optical base 100. Positioning of the plate 101 is, for example, based on guide pins 103 which are fixed on the optical base 100. The pins 103 are assumed to be adjusted relatively to the optical axis of the optical system. The plate 102 is fixed to the plate 101. The illumination light source 3 needs to be replaced when the life span of laser oscillator expires. In order to minimize the down-time of the apparatus when the illumination light source 3 is replaced, the light source 3 undergoes the optical axis adjustment prior to the placement on the plate so that it exerts the intended performance following the minimal adjustment of optical axis.

Figure 6A:
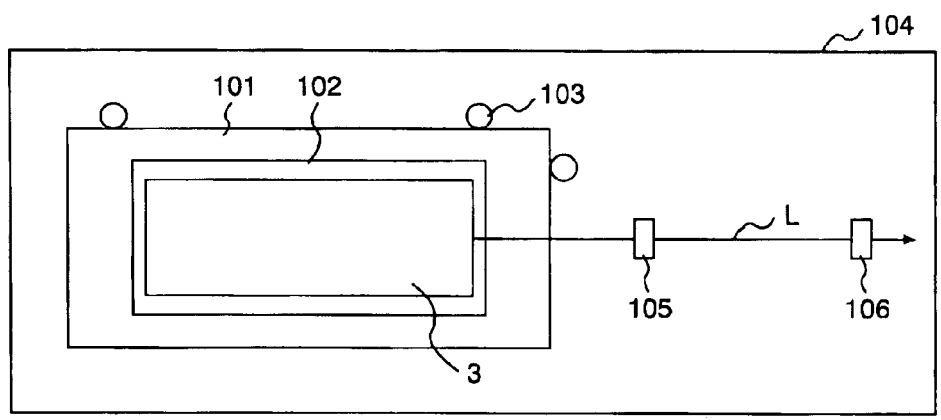
FIG. 6A is a front view of the illumination light source, showing the manner of adjustment of the laser light source based on this invention.
Figure 6B:
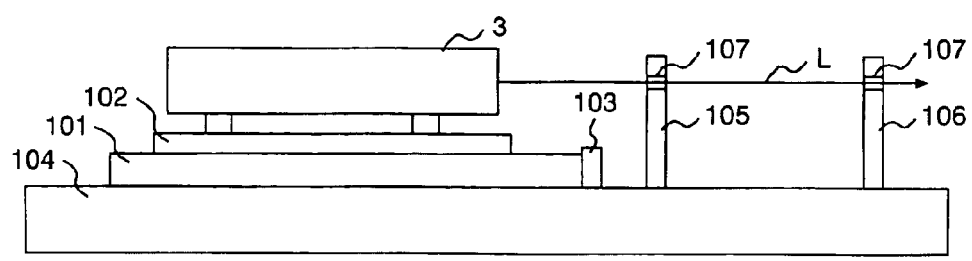
FIG. 6B is a plan view of the light source.

FIGS. 6A and 6B show by plan view and side view, respectively, an example of optical axis adjustment devices. On an optical axis adjustment base 104, the positioning pins 103 are fixed in the same layout as the optical base 100. Targets 105 and 106 having the same height and having the formation of pin-holes 107 for transmitting a laser beam are fixed on the base 104 by being aligned in parallel to the alignment of pins 103. The targets 105 and 106 are spaced out by a distance which is enough to adjust the laser light source 3. The plate 101 is fixed to the optical axis adjustment base 104. The illumination light source 3 is fixed temporarily on the plate 102 in advance. With the plate 102 being placed on the plate 101, the laser source is activated to emit a laser beam. The position of the plate 102 is adjusted in the right/left direction and the laser source is adjusted in the inclination direction so that the laser beam L goes through the pin-holes 107. Following the adjustment, the illumination light source 3 is fixed to the plate 102, and the plate 102 is fixed to the plate 101. In consequence, the illumination light source 3 has its laser beam adjusted based on the position of the pins 103. The illumination light source 3 fixed on the plate 101 is moved from the adjustment base 104 to the optical base 100, resulting in a consistent optical axis before and after the replacement of light source.

Figure 7A:
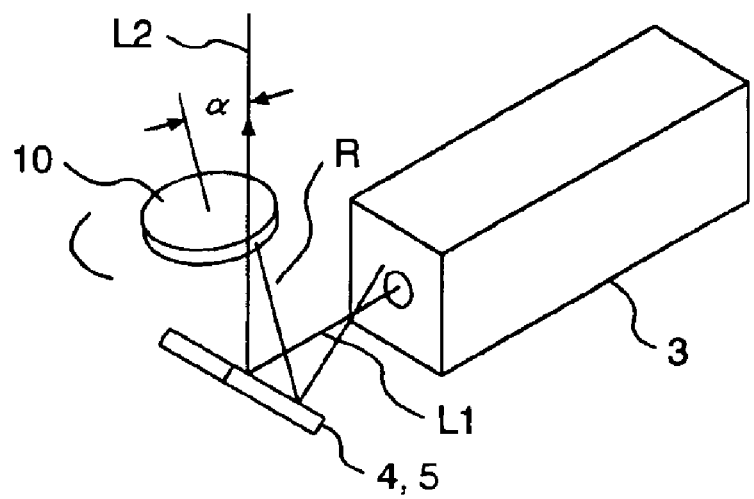
FIG. 7A is a perspective view of the optical system including the ND filter and illumination light source based on this invention.
Figure 7B:
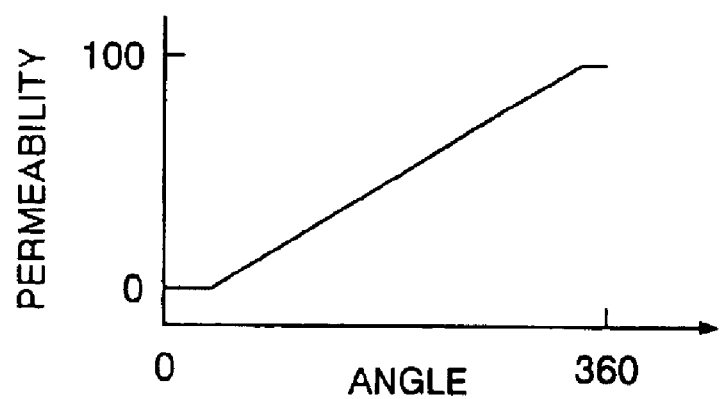
FIG. 7B is a graph showing the characteristics of the light quantity adjusting mechanism.

Next, the ND filter 10 which limits the light quantity will be explained. The illumination light source 3 emits a laser beam at the maximum output, and it is necessary to limit the quantity of light which reaches the image sensor 20. An ND filter 7 is placed to cut in the light path. FIG. 7A shows the disposition of the ND filter 10, and FIG. 7B shows its characteristics. The ND filter 10 varies in transmissivity depending on the angle as shown in FIG. 7B. The ND filter 10 can be swung and fixed at an intended angle in a certain manner (not shown). The ND filter 10 has such an angle α relative to the optical axis that the reflected laser beam R from the filter 10 does not return directly to the laser emission port of the illumination light source 3. The basis of this angle setting is to prevent the instability of the laser output due to the interference of the reflected beam from the ND filter 10 with the beam in the resonator of the illumination light source 3.

Next, the limiting aperture system will be explained. FIGS. 8A and 8B show examples of limiting aperture 13. The limiting aperture 13 is conjugate in position with the pupil 14a of the objective lens 14. For the pupil 14a having a maximum diameter of d, the limiting aperture 13 can vary the light transmission diameter d1 depending on the pattern shape on the surface of the subject 1. The limiting aperture 13 may be design to provide a ring-shaped aperture as shown in FIG. 8B to accomplish the ring-shaped illumination. For the pupil 14a having a maximum diameter of d, the limiting aperture 9a performs the ring-shaped light transmission having an inner diameter of d2 and outer diameter of d3. By preparing limiting apertures having several sets of diameters and changing the limiting aperture in a certain manner (not shown), imaging at the higher resolution can be accomplished.

Next, the illumination will be explained.

FIGS. 9A and 9B show the illumination state of the objective lens pupil 32 and the view field 33, respectively, resulting from the illumination of the ordinary white light. A light source image 34 is focused at the position of the pupil 32, while the whole view field 35 is illuminated virtually uniformly at the position of the view field 33.

Figure 10A:
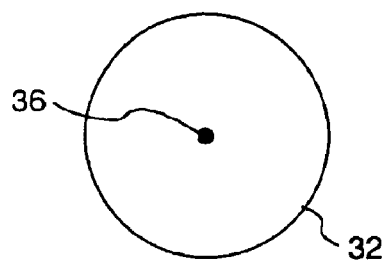
FIG. 10A is a plan view showing the state of laser illumination on the pupil of imaging objective lens.
Figure 10B:
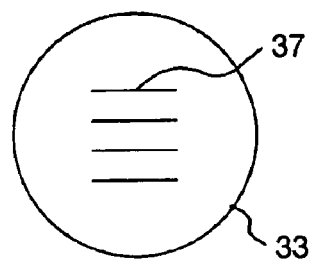
FIG. 10B is a plan view showing the state of laser illumination on the pupil of imaging objective lens.
Figure 10C:
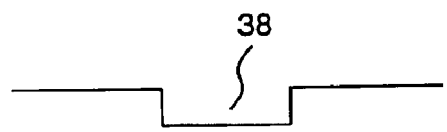
FIG. 10C is a cross-sectional diagram of a pattern.
Figure 10D:
FIG. 10D is an imaging waveform diagram.

FIGS. 10A–10D show the illumination state resulting from a laser light source. A light source image 36 having a shape of light spot is focused at the position of the pupil 32 as shown in FIG. 10A. A circuit pattern which has a cross section as indicated by 38 in FIG. 10C and is illuminated in the view field 33 as indicated by 37 in FIG. 10B results in a detected waveform 39 as shown in FIG. 10D. When the circuit pattern is imaged by the illumination of laser light, there arise overshooting and undershooting at the pattern edge and there also emerge speckles 40. The cause of these waveforms is a small Γ of illumination. It implies that the view field 33 beneath the objective lens 14 is not illuminated at multiple angles. Illumination of the ordinary white light has a certain beam size on the pupil 32 and has a range of illumination angles comparable to the NA (numeral aperture) of the objective lens 14 against the view field 33.

Figure 11A:
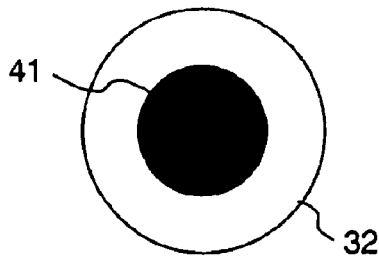
FIG. 11A is a plan view showing the state of laser illumination on the pupil of imaging objective lens.
Figure 11B:
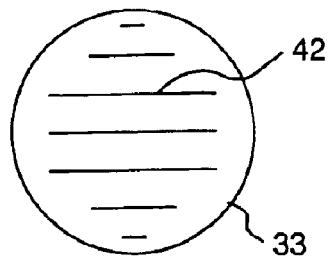
FIG. 11B is a plan view showing the state of laser illumination in the view field.

Coherent lights such as the laser have a value of σ (it is proportional to the size of light source on the pupil) of zero, since the point light source of coherent light results in a point image at the pupil. Although it is feasible to produce an expanded light beam 41 with another lens system and cast onto the pupil 32 as shown in FIG. 11A, the result is the same as if the whole light come from a position of σ=0 (indicated by 39 in FIG. 10D), and the problem is left unsolved. On this account, it is necessary to have a means of diminishing the coherency, i.e., time coherency or spatial coherency, of the laser beam.

Figure 12A:
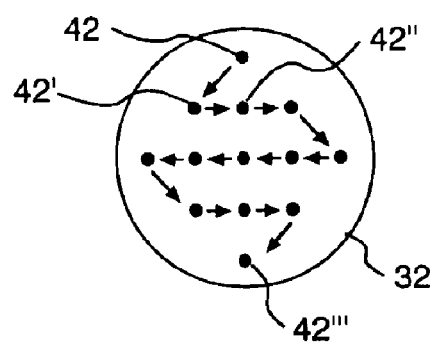
FIG. 12A is a plan view showing the state of laser illumination on the pupil of imaging objective lens.
Figure 12B:
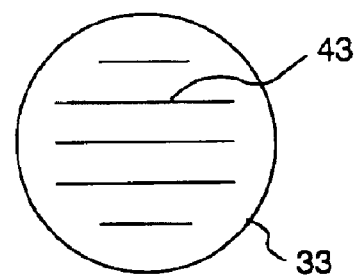
FIG. 12B is a plan view showing the state of laser illumination in the view field.
Figure 12C:
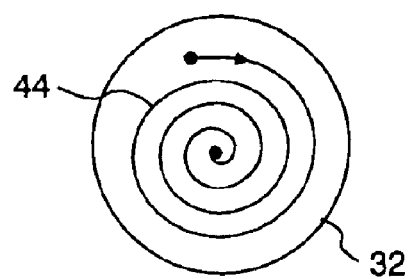
FIGS. 12C and 12D are plan views showing the state of laser illumination on the pupil of imaging objective lens.
Figure 12D:
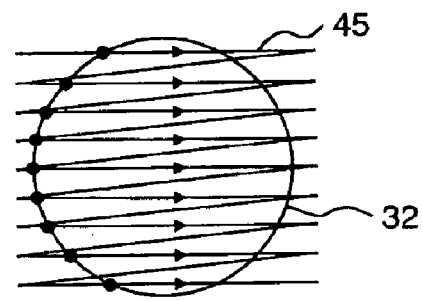

Next, an embodiment of coherency diminishment will be explained. The invention proposes the operation in which the light source image is focused on the pupil 32, a position 42, for example, in FIG. 12A is illuminated at first, and subsequently positions 42' and so on are scanned sequentially, thereby illuminating, as indicated by 43, the view field 33 as shown in FIG. 12B. The pupil 32 may be scanned in a spiral fashion as indicated by 44 in FIG. 12C, or maybe scanned in a 2-dimensional fashion 45 as shown in FIG. 12D. Although images of speckles, overshooting and undershooting are created at positions, they do not interfere with each other due to different timings of imaging. Summing these images by the image sensor 20 results in a same image derived from a coherent light source.

For the summation of images, the image sensor 20 is preferably of the accumulation type such as CCD (specifically, TDI sensor) having a pixel size of 0.05–0.3 μm in terms of dimension on the subject (view field). Among various CCD sensors, the image sensor 20 is of the TDI (time delay and integration) type. The TDI sensor is a 1-dimensional sensor in which N pieces of (several tens to 1000) photosensors called "stages" are aligned in the lateral direction and multiple stages are aligned in the longitudinal direction. The sensor allows arbitrary control of drive frequency.

Figure 13:
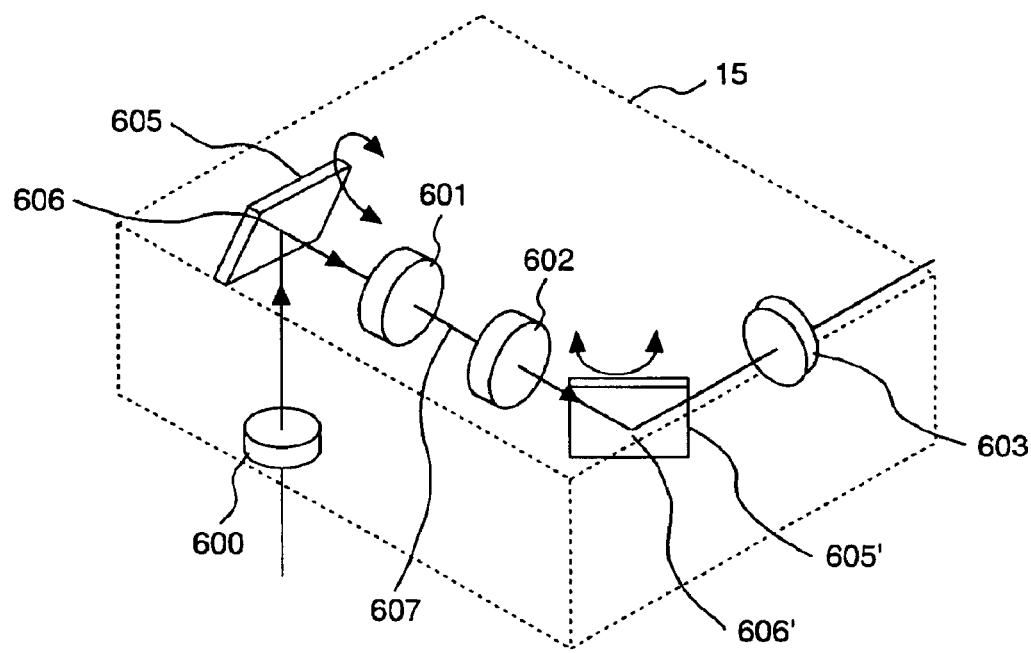
FIG. 13 is a perspective view of the illumination light path switching optical system based on this invention.

Next, an embodiment of coherency diminishment 15 based on the scanning of light source image will be explained. FIG. 13 shows the arrangement of the coherency diminishing optical system 15 using a scanning means of a resonance-type galvanomirror. A lens 600 makes a light beam illuminated from the illumination light source 3, at a position 606 which is conjugate with the pupil 14a of the objective lens 14. Lenses 601 and 602 make a reflected light beam at a next conjugate position 606'. A lens 603 focuses the reflected light beam on the pupil 14a of the objective lens 14. A galvanomirror 605 which can swing in the up/down direction is disposed at the conjugate position 606, and another galvanomirror 605' which can swing in the right/left direction is disposed at the conjugate position 606'. A position 607 conjugate with the subject 1 is set between the lens 602 and the lens 603.

Figure 14:
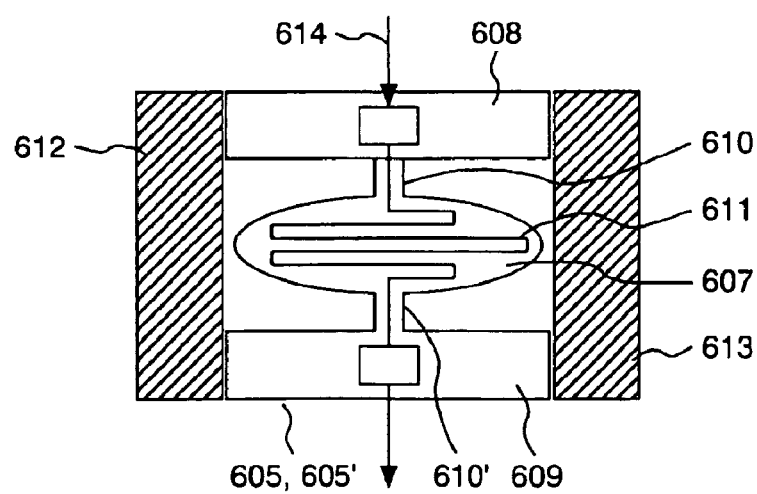
FIG. 14 is a front view of the resonance-type galvanomirror based on this invention.

FIG. 14 shows an embodiment of resonance-type galvanomirror. The galvanomirrors 605 and 605' are each made by integrated fabrication inclusive of a stationary portion and swing portion. The galvanomirror has a swing flat 607 which is supported by bars 610 and 610' extending from stationary members 608 and 609. The flat 607 has the formation of a coil 611. There are magnets 612 and 613 on both sides of the coil 611. The coil 611 is supplied with a current 614, and it reacts against the magnets 612 and 613, causing the flat 607 to swing. The flat 607 has its rear surface coated to behave as a mirror so that the laser beam is totally reflected.

Figure 15:
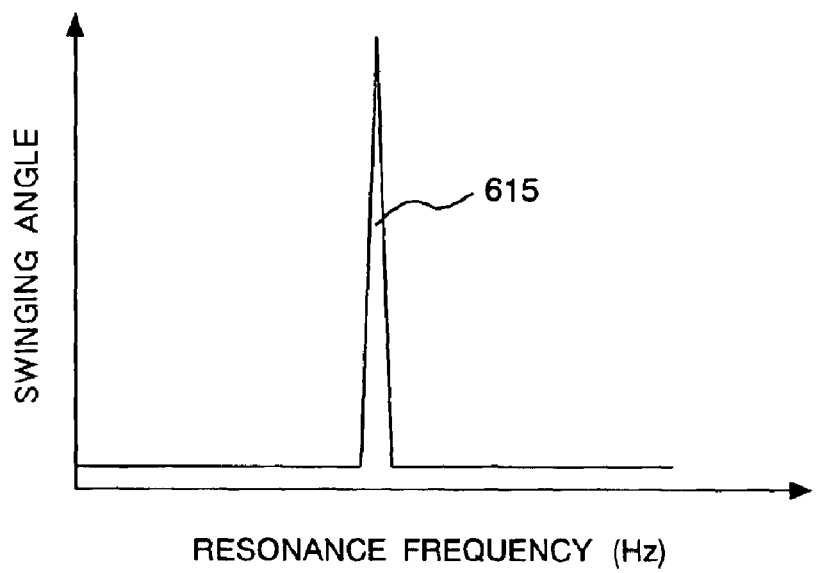
FIG. 15 is a graph showing the frequency characteristics of the resonance-type galvanomirror based on this invention.
Figure 16:
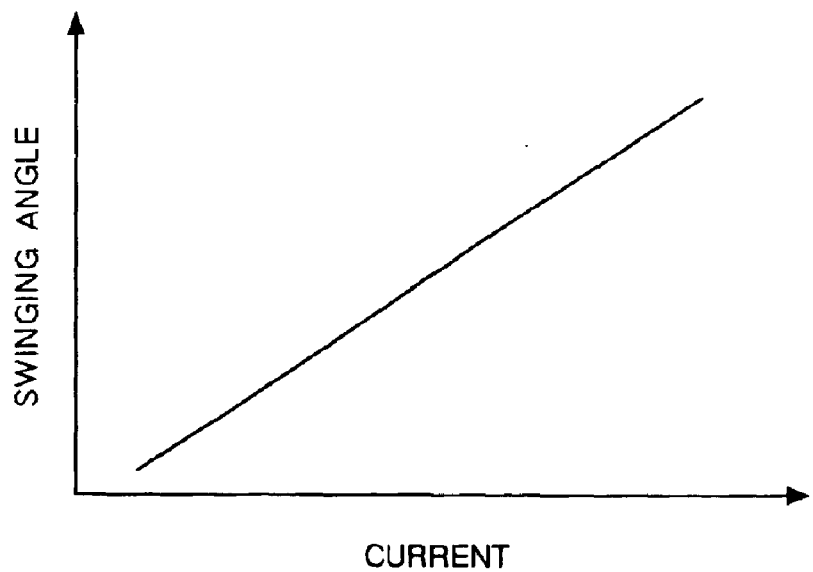
FIG. 16 is a graph showing the relation between the supply current and the swing angle of the resonance-type galvanomirror based on this invention.

The flat 607 can be confirmed to swing at a constant frequency by supplying with a certain amount of current to the coil 611. FIG. 15 shows the frequency characteristics 615 plotted along the horizontal axis of resonance frequency and the vertical axis of swing angle. The frequency which makes a peak swing angle can be set arbitrarily between 1000 Hz and 5000 Hz by adjusting the width of the bars 610 and 610'. Frequencies below 1000 Hz are also attainable obviously. The galvanomirror is designed so that the swing angle is maximal at the intended frequency. FIG. 16 shows the relation between the current value and the swing angle plotted along the horizontal axis of current and the vertical axis of swing angle. The swing angle can be limited based on the amount of current supplied. The galvanomirrors disposed as shown in FIG. 13 operate to swing the light beam horizontally and vertically, and the use of galvanomirrors having the same resonance frequency is desirable.

The resonance frequency of galvanomirror is preferably tuned to the accumulation time of the image sensor 20. The image sensor 20 gets images in a cycle time which is the product of the drive frequency and the number of stages in the lateral direction. For example, in the case of a 300-kHz drive frequency and 500 stages, it images at a frequency of 600 Hz. By setting the characteristics of the resonance-type galvanomirror to have a swing frequency of 600 Hz, the swing motion of one rotation can be accomplished in the accumulation time. In case the resonance-type galvanomirror has its characteristic frequency deviated to, such as 611 Hz, from the ideal frequency due to the disparity of fabrication process or the like, the swing motion of one rotation in the accumulation time can be accomplished by altering the image sensor drive frequency to 305.5 kHz. Namely, based on the adjustment of either the image delivery time to the image sensor or the frequency of resonance-type galvanomirror, it is possible to have the ideal swing motion and imaging.

Next, a second embodiment of coherency diminishment will be explained. In this embodiment, a diffusion plate is placed on the laser light path, by which the incident angle is shifted in a time fashion thereby to diminish the coherency.

Figure 17:
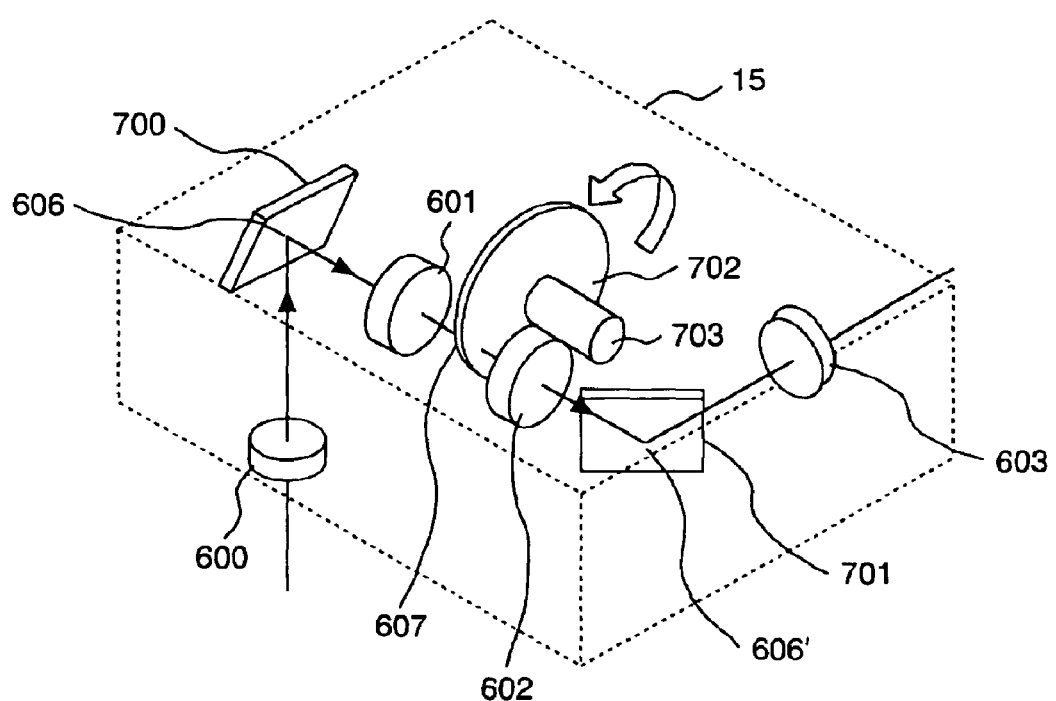
FIG. 17 is a perspective view of the illumination light path switching optical system based on this invention.

FIG. 17 shows the arrangement of the coherency diminishing optical system 15. The light beam from the illumination light source 3 is conducted through a lens 600 to reach a position 606 which is conjugate with the pupil 14a of the objective lens 14. The reflected light beam is conducted through lenses 601 and 602 to reach a next conjugate position 606'. A lens 603 focuses the reflected light beam on the pupil 14a of the objective lens 14. Mirrors 700 and 701 are placed at the conjugate positions 606 and 606'. A position 607 conjugate with the subject 1 is established between the lens 602 and the lens 603. A diffusion plate 702 which is rotated by a motor 703 is placed near the conjugate position.

Figure 18A:
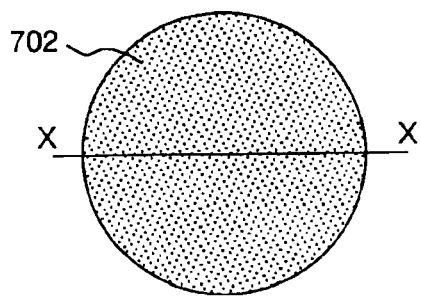
FIG. 18A is a front view of the diffusion plate of the coherency diminishing optical system based on this invention.
Figure 18B:
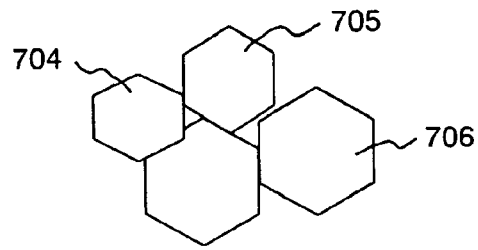
FIG. 18B is an enlarged front view of the diffusion plate.
Figure 18C:
FIG. 18C is a cross-sectional diagram of the diffusion plate taken along the x—x line of FIG. 18A.

FIG. 18A shows a front view of the diffusion plate 702, FIG. 18B shows the details of the diffusion surface, and FIG. 18C shows the cross section taken along the X—X line of FIG. 18A. The diffusion plate 702 has preferably a random layout of particles 704, 705, 706 having a polygonal or circular shape and having random sizes around 0.1 mm in terms of surface observation. The particles are preferably random also in cross-sectional shape and size.

Figure 19:
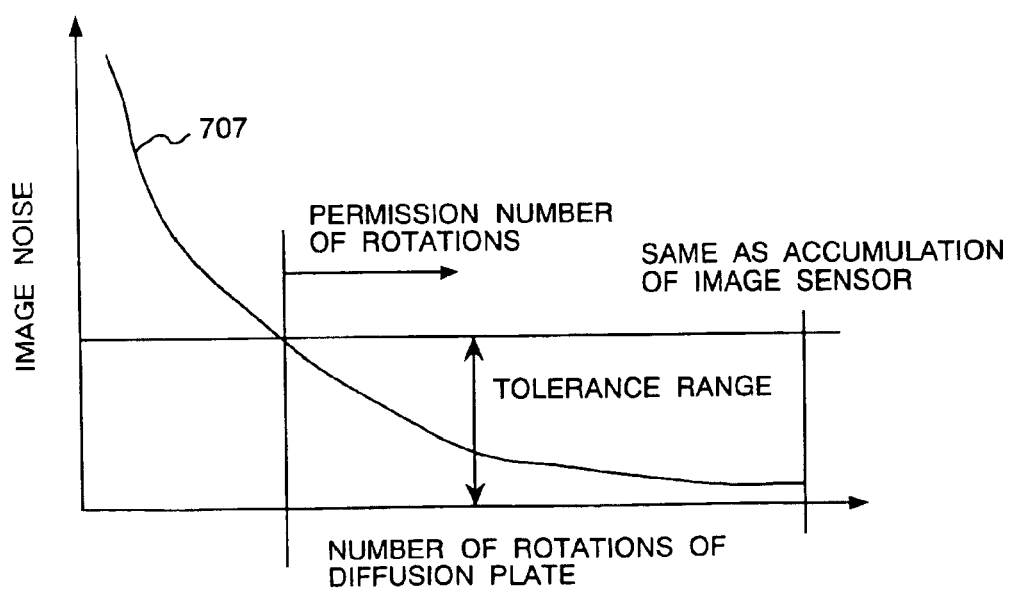
FIG. 19 is a graph showing the relation between the rotational speed and the image noise of the coherency diminishing optical system based on this invention.

The diffusion plate 702 is preferably driven to rotate once in the accumulating time of the image sensor 20. However, this rotational speed will be infeasible due to the accumulating time of the image sensor 20 of the order of several hundreds Hertz. An experiment was conducted to assess the relation between the rotational speed of diffusion plate and the noise of image sensor, with the result 707 being plotted along the horizontal axis of diffusion plate rotational speed and the vertical axis of image sensor noise on the graph of FIG. 19. The noise was defined to be the fluctuation of brightness of the image sensor which receives a reflected light from a subject of flat surface without exposing a circuit pattern. The noise level is smallest at the point where the rotational speed of diffusion plate matches with the accumulating time of image sensor. The basis of this fact is for being averaged by one revolution of particles 704 on the diffusion plate 702 in the accumulating time of the image sensor 20. The noise level decreases in a fashion of second-degree function, and at noise levels which do not affect the performance of image processing, it is not compulsory to equalize the one-revolution time of diffusion plate to the accumulating time of image sensor. This critical rotational speed is around 12000 rpm. Accordingly, the effect of noise level reduction can be attained by simply rotating the diffusion plate 702 with a conventional means.

Figure 20A:
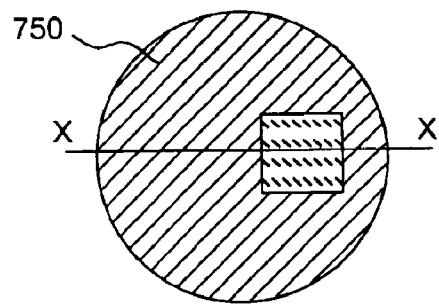
FIG. 20A is a front view of the phase plate of the coherency diminishing optical system based on this invention.
Figure 20B:
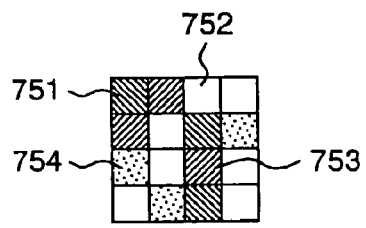
FIG. 20B is an enlarged front view of the phase plate.
Figure 20C:
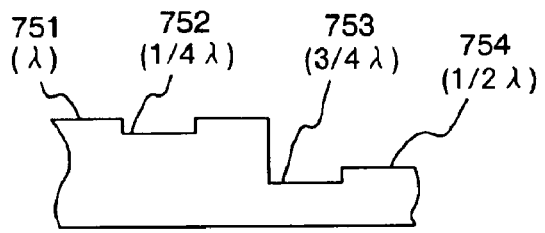
FIG. 20C is a cross-sectional diagram of the phase plate taken along the x—x line of FIG. 20A.

The same effect is attained when the diffusion plate 702 is replaced with a phase plate. FIG. 20A shows a front view of a phase plate 750, FIG. 20B shows the details, and FIG. 20C shows the cross section taken along the X—X line of FIG. 20A. The phase plate 750 is stepped in width in terms of random phase shift to have a random layout of a segment 751 of phase λ, a segment 752 of ½ λ phase shift, a segment 753 of ¼ λ phase shift, a segment 754 of ¾ λ phase shift, and so on. The phase plate 750, in place of the diffusion plate 702, is fixed to and is rotated by the motor 703 so that the laser beam varies in phase in response to the depth of steps, and the coherency of laser can be diminished.

The same effect is attained obviously when the diffusion plate and resonance-type galvanomirror are placed on the same light path.

Figure 21:
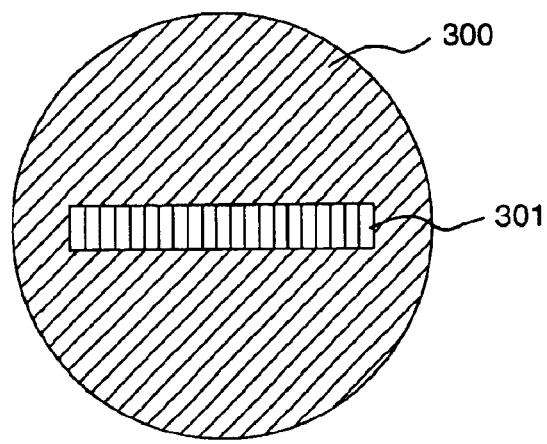
FIG. 21 is a plan view showing the illumination area in the view field.
Figure 22:
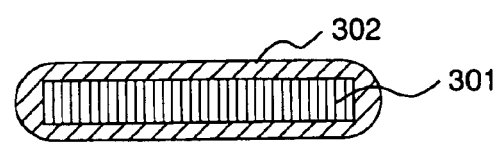
FIG. 22 is a plan view showing the relation between the CCD detector and the illumination area in the view field based on this invention.

Next, the range of illumination will be explained. FIG. 21 shows the concept of illumination. Generally, illumination of a microscope or the like is the circular illumination 300 on the subject. However, in the case of using a 1-dimensional image sensor as employed by the inventive apparatus, only an elongated range 301 on the subject contributes to imaging, leaving other useless illuminated area. In order to raise the luminous intensity for the imaging by the image sensor, elongated illumination as shown by an area 302 in FIG. 22 is suitable for the imaging range 301 of the image sensor. A TV camera used for observation necessitates a rectangular illumination range, which cannot be covered entirely by the above-mentioned elongated illumination.

Figure 23A:
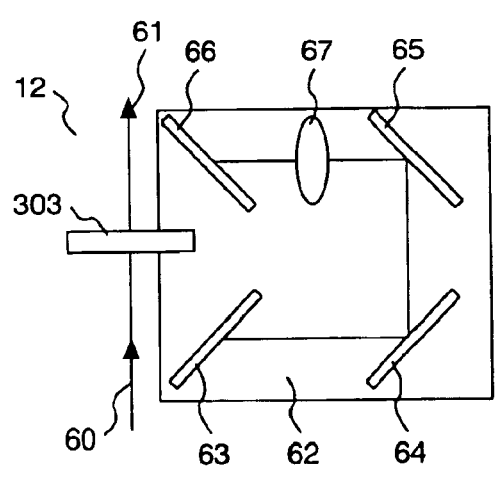
FIG. 23A is a plan view showing the configuration of the illumination light path switching optical system at the inspection based on this invention.
Figure 23B:
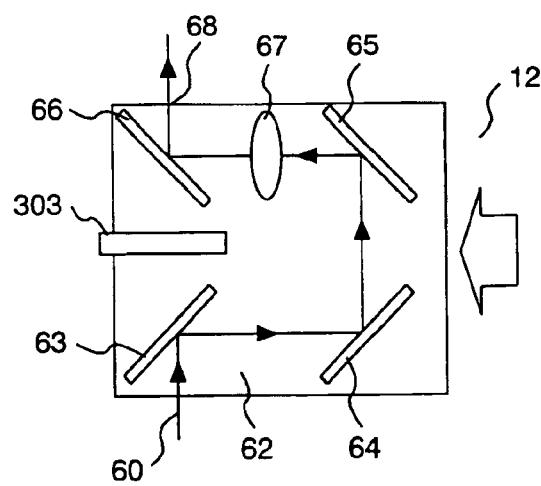
FIG. 23B is a plan view showing the configuration of the illumination light path switching optical system at the observation with a TV camera.

Next, the illumination light path switching optical system 12 will be explained. FIGS. 23A and 23B show the arrangement of this optical system 12. The illumination light from the illumination light source 3 has a light path 60, on which is placed a homogenizer 303. Mirrors 63, 64, 65 and 66 and a lens 67 are fixed to a base 62. The base 62 is movable in a certain manner (not shown) toward the light path 60. Shown by FIG. 23A is the state of inspecting by the image sensor 20, with illumination being achieved by the homogenizer 303. Shown by FIG. 23B is the state of observation with a TV camera 27, in which case the base 62 is moved to insert in the light path 60. In this state, the light path 60 of illumination runs to the light path 68 through the mirrors 63, 64, 65 and 66 and the lens 67, and the ordinary circular illumination can be provided.

Figure 24:
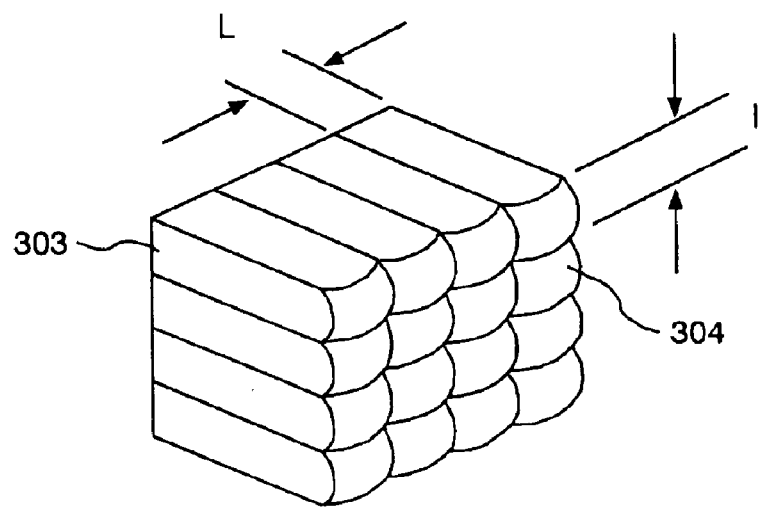
FIG. 24 is a perspective view of the homogenizer based on this invention.

Next, the homogenizer which accomplishes the elongated illumination will be explained. FIG. 24 shows the shape of the homogenizer 303. The homogenizer 303 is arranged a plurality of lens arrays 304. Each lens array 304 is arranged so as to image at the pupil 14a of the objective lens 14 through a set of lenses placed on the light path. The each lens array 304 has a rectangular shape (L×I). A longish direction of the rectangular illumination is matched a longish direction of each lens array 304. By arranging a plurality of this lens arrays, the intended rectangular illumination 302 is accomplished.

Figure 25:
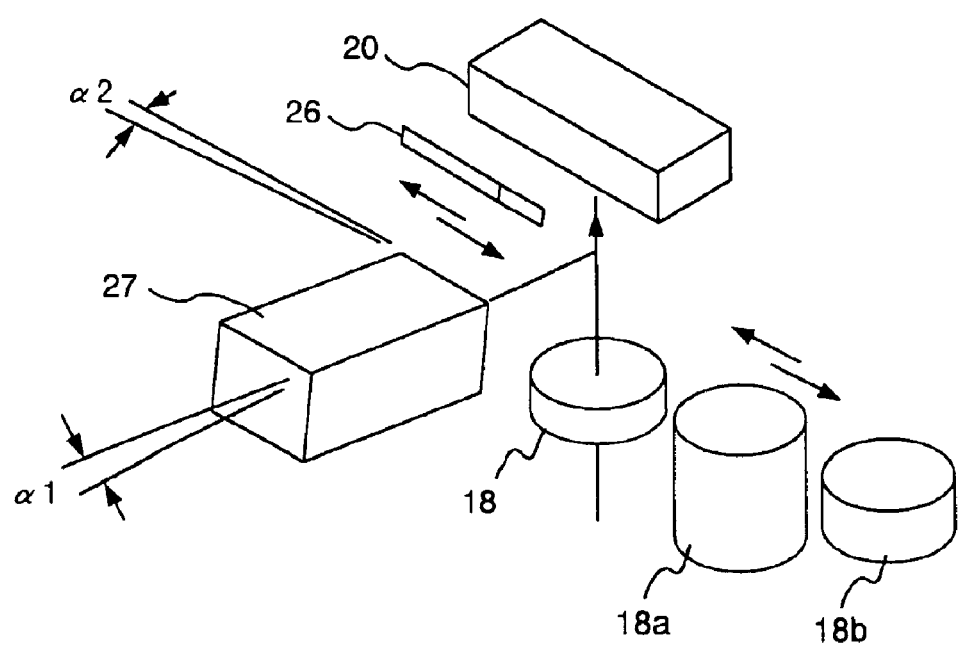
FIG. 25 is a perspective view showing in brief the structure of the imaging light path switching mechanism based on this invention.

Next, the illumination light path switching mechanism will be explained. FIG. 25 shows this mechanism 26, 18. The illumination light path switching mechanism functions to switch the light path for the image sensor 20 and TV camera 27. A mirror 26 is adapted to insert in the light path in a certain manner (not shown). With the mirror 26 being located on the light path, the TV camera 27 is fixed at the position conjugate with the imagery position of the image sensor 20. The mirror 26 is retracted from the light path when the image sensor 20 is inspected the image of the subject (the specimen) 1. At the observation of inspection result, the mirror 26 is moved to insert in the light path in a certain manner (not shown), and the subject 1 can be observed with the TV camera 27. The TV camera 27 is attached with a certain angle for the light axis.

The TV camera 27 generally places a glass cover in front of a sensor with the intention of protecting the sensor. If a laser beam carries out incidence to the front and rear surface of this glass cover, multiplex interference will occur. Therefore, interference fringes will occur on an observation screen of the sensor. On this account, angles α1 and α2 of the TV camera 27 are adjusted before fixing so that the emergence of interference fringes is prevented. The camera 25 is also fixed to have a certain angle.

Another mirror 23 has the same function as the mirror 26. A variety of imagery lenses 18 of different magnifications are used selectively depending on the pixel size. For a different pixel size, the imagery lens is replaced, instead of the objective lens. Imagery lenses 18a and 18b of different magnifications have the same imagery position. Consequently, the image sensor 20 and TV camera 27 do not need to be relocated at the change of magnification, enabling the stable imaging operation.

The magnification is determined by the focal distance of the objective lens 14 and the focal distances of the imagery lenses 18, 18a and 18b, and the pixel size is determined by the aperture size of the image sensor 20. The magnification can possibly fluctuate among production lots of optical system due to the fabrication error of the objective lens 14 and imagery lenses 18, 18a and 18b and also their assembling error, and the difference of magnification results in different sensitivities of imaging among production lots of optical system, i.e., among apparatus. On this account, the imagery lenses 18, 18a and 18b are provided with a mechanism for making their focal distances adjustable.

Figure 26:
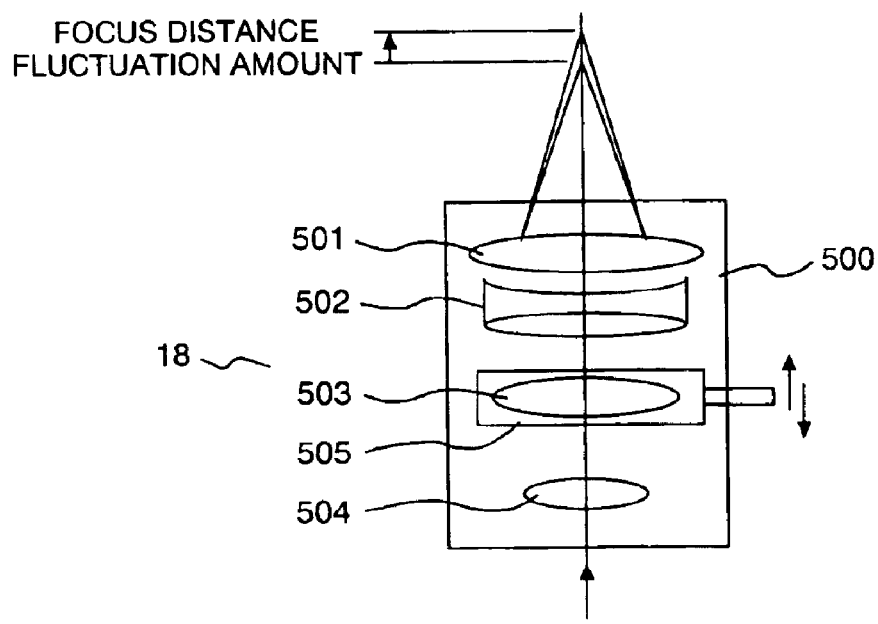
FIG. 26 is a plan view of the imagery lens system based on this invention.

FIG. 26 shows the cross section of an imagery lenses. The imagery lens 18 is made up of multiple lenses 501, 502, 503 and 504 combined in an optical tube 500. The imagery lens 18 is designed to have variable focal distance based on, for example, the movement of one of the lens set. In the example shown, the focal distance is varied by the movement of the lens 503. The lens 503 is framed in a lens holder 505 so that it can be operated for movement from the outside of the optical tube 500. The lens holder 505 is moved in a certain manner (not shown) to vary the focal point (focal distance) of the lens 18. With the objective lens 14 having a constant focal distance, the magnification can be varied. Using a zoom lens for the imagery lens with the ability of variable magnification achieves the same effect obviously.

Figure 27:
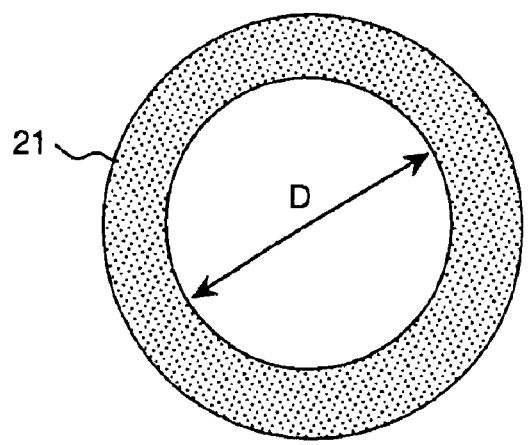
FIG. 27 is a plan view of the diaphragm based on this invention.

Next, the diaphragm 21 will be explained. FIG. 27 shows an embodiment of the shape of the diaphragm 21. The diaphragm has its light transmission range D set equal to the size of the pupil 14a. The diameter D is varied by the control system 22 in a certain manner (not shown) to control (adjust) the light transmission range.

Based on the combination of the diameter D and the swing range of the resonance-type galvanomirror of the coherency diminishing optical system 15, it is possible to control the diffracted light from the pattern of the subject 1 and put in to the image sensor 20.

Figure 28A:
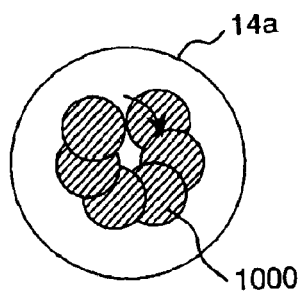
FIG. 28A is a plan view of the pupil, showing the illumination locus on the pupil of objective lens based on this invention.
Figure 28B:
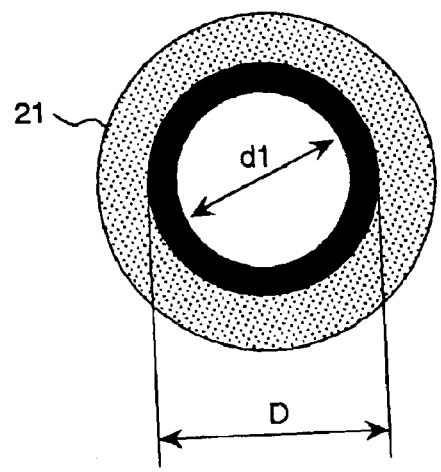
FIG. 28B is a plan view of the diaphragm, showing the control range of diaphragm.

FIGS. 28A and 28B show an example of this affair. Shown by 28A is the locus of illumination 1000 in the pupil 14a of the objective lens 14, and shown by FIG. 28B is the control range of the diaphragm 21. The control range is determined in terms of diameter d1 so that the high-order components of diffracted light can be controlled. This combination is effectual for the grain and the like existed on the surface of the subject 1.

Figure 29A:
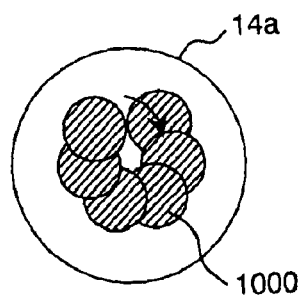
FIG. 29A is a plan view of the pupil, showing the illumination locus on the pupil of objective lens based on this invention.
Figure 29B:
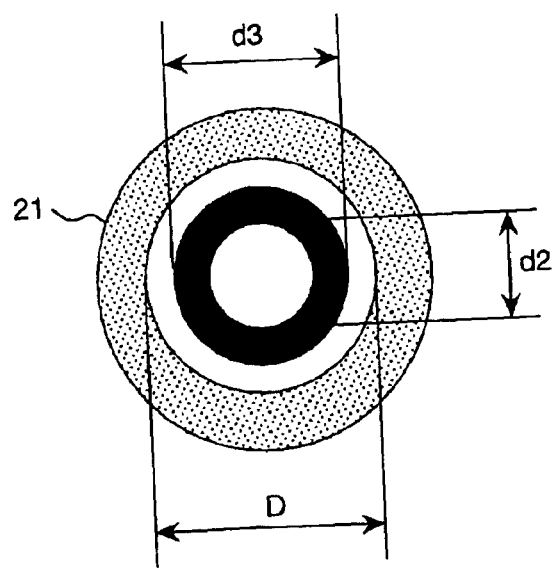
FIG. 29B is a plan view of the diaphragm, showing the control range of diaphragm.

FIGS. 29A and 29B show another example of the affair. Shown by 29A is the locus of illumination 1000 in the pupil 14a of the objective lens 14, and shown by FIG. 29B is the control range of the diaphragm 21. The control range is determined in terms of diameters d2 and d3 so that the major component of diffracted light from the subject 1 can be controlled. This combination is effectual for the irregularity of color and the like existed on the surface of the subject 1.

Figure 30:
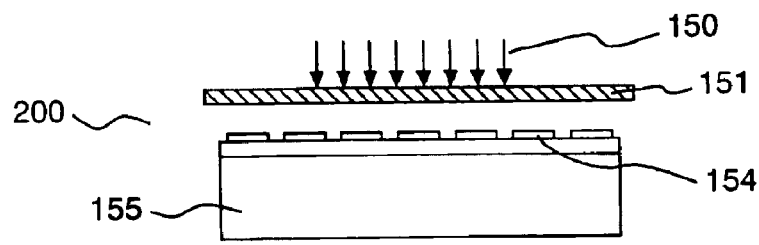
FIG. 30 is a side view of the TDI image sensor based on this invention.

Next, an embodiment of the TDI sensor which is sensitive to the UV light, particularly the DUV light, will be explained. FIG. 30 shows a sensor of the surface reflection type. In the case of using the DUV laser for the illumination light source 3, an image sensor which is sensitive to the DUV light must be used. In the surface-reflective image sensor 200, the incident light 150 goes through a glass cover 151, passes through a gate 154, and enters a CCD 155, causing incident light components of short wavelengths to be attenuated. The sensor is almost insensitive to wavelengths of 400 nm or less, and is not capable of detecting the DUV light effectively. There is a scheme for coping with this matter, in which the glass cover is coated with an organic thin film which radiates visible light in response to the incident of DUV light, and consequently an image sensor which is sensitive only to the visible light can sense the DUV light.

Figure 31:
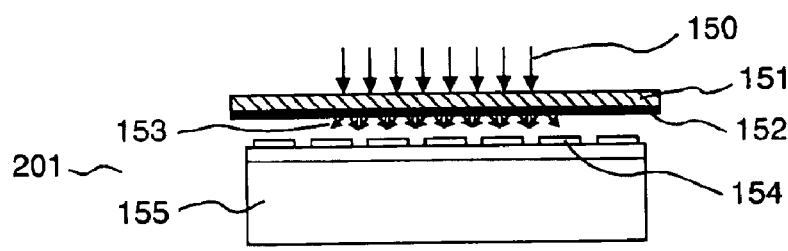
FIG. 31 is another side view of the TDI image sensor based on this invention.

FIG. 31 shows an image sensor based on the scheme of organic thin film coating. The image sensor 201 of this scheme has its glass cover 151 coated with a organic thin film 152, which radiates the fluorescent light 153 in response to the incident light 150 transmitted through the glass cover 151 on the coated surface of the organic thin film 152, enabling an image sensor of the surface illumination type, which is only sensitive to the visible light, to sense the DUV light.

Figure 32:
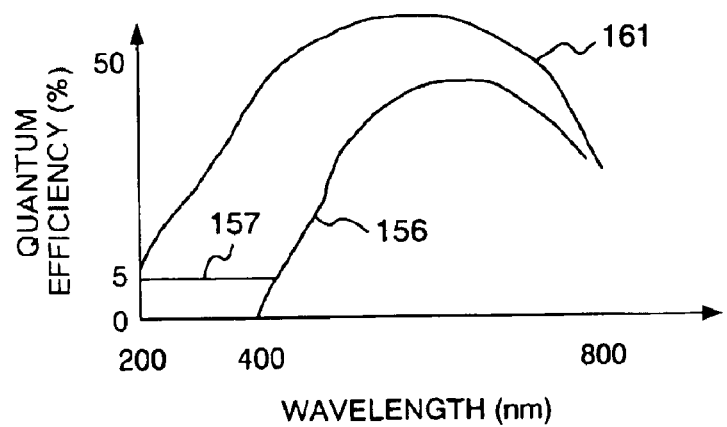
FIG. 32 is a graph showing the spectral characteristics of the TDI image sensor based on this invention.

FIG. 32 shows spectral characteristics of image sensors. Spectral characteristics 156 are of the ordinary image sensor 200 of the surface illumination type, and this sensor has no sensitivity to wavelengths of 400 nm or less. Spectral characteristics 157 are of the image sensor 201 having an organic thin film coating, and this sensor has the rendition of additional sensitivity to wavelengths of 400 nm or less.

Figure 33:
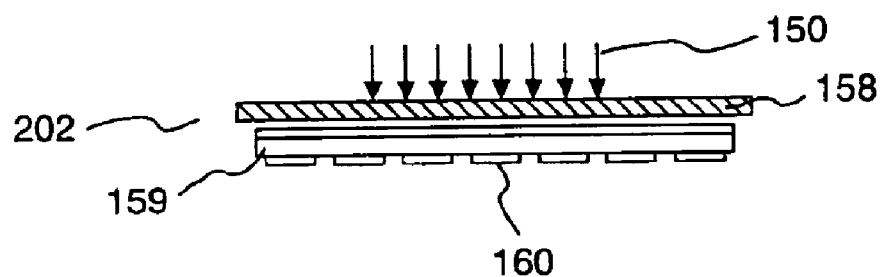
FIG. 33 is a side view of the TDI image sensor of the back illumination type based on this invention.

For having much higher sensitivity to the DUV light, an image sensor of the rear-surface irradiation type should be used. FIG. 33 shows the structure of this image sensor. The incident light 150 are transmitted through a glass cover 158 and incident to the rear surface 159 without a gate structure. The incident light do not go through the gate 160 and therefore have spectral characteristics 161 shown in FIG. 32. This image sensor has a high quantization factor (e.g., 30% or more) and a wide dynamic range (e.g., 3000 or more) and is sensitive to wavelengths of 400 nm or less, and it is particularly advantageous for the illumination of short wavelengths such as 200 nm or less. This type of image sensor is capable of dealing with several wavelengths of illumination. By designing the image sensor 20 to be of the TDI (time delay integration) type, the sensitivity can be raised. By designing the image sensor 20 to have the anti-blooming characteristics, it is possible to overcome the problem of overflowing charges to neighboring pixels at the input of excessive light quantity.

Figure 34:
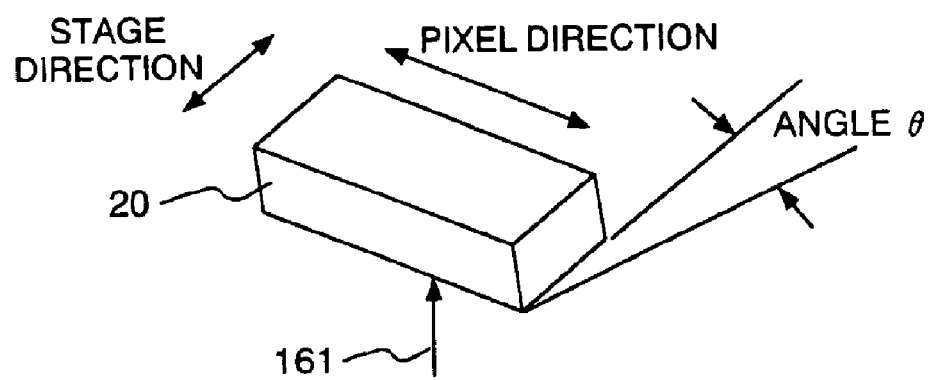
FIG. 34 is a perspective view of the TDI image sensor, explaining the manner of attachment of the TDI image sensor based on this invention.

Next, the fitting of the image sensor 20 will be explained. FIG. 34 shows the manner of fitting of the sensor. The image sensor 20 has a glass cover as mentioned previously, and therefore interference fringes can possibly emerge on the glass surface. By inclining the sensor 20 by angle θ against the direction of stages, it is possible to prevent the emergence of interference fringes caused by the interference of laser, while being free from the occurrence of out-focusing in the direction of pixels.

Next, a scheme of improving the contrast of pattern based on the control of a set of polarizing devices 17 which have been mentioned previously, in addition to the enhancement of resolution by use of the UV light, will be explained. Based on the fact that the state of polarization of UV laser can be manipulated by controlling the polarizing devices 17 with the intention of improving the pattern contrast, it becomes possible to detect partially-polarized light components with the image sensor 20 by controlling the direction of polarization of illumination light and the elliptic factor. Illumination by UV laser is characterized by having a single wavelength and linear polarization. Therefore, the state of polarization can be controlled efficiently by use of the polarizing devices 17 including a halfwave plate and quarterwave plate placed on the light path. Specifically, the halfwave plate and quarterwave plate are rotated about the optical axis.

The pattern contrast varies significantly depending on the state of polarization of illumination, and accordingly the performance of optical system can be enhanced by making the polarization state controllable (positioning of the wave plate by rotation). More specifically, the direction of linear polarization is controlled with the halfwave plate, and the elliptic factor is controlled with the quarterwave plate. In consequence, the sensitivity of detection can be enhanced. Based on the combination of these plates, a parallel Nicol and orthogonal Nicol can be accomplished. The state of circular polarization can also be accomplished obviously. These byproducts are not dependent on the wavelength of illumination. Means of accomplishment is arbitrary, provided that the above-mentioned concept is satisfied. The polarization control means 17 includes one or both of the quarterwave plate or the halfwave plate and the quarterwave plate disposed on the light path ranging from the UV light source 3 up to the subject 1, and an analyzer (not shown) disposed on the light path of the light reflected by the subject ranging from the subject 1 up to the detector of said image detecting means 20. Controlling the polarization enables the efficient detection of high-order diffracted light. An experiment conducted by the inventors of the present invention reveals that the contrast is improved by about 20–300%.

According to the foregoing setup of optical system, the illumination light (e.g., UV laser) coming out of the illumination light source 3 is reflected by the mirrors 4 and 5, transmitted through the ND filter 7 which limits the quantity of light, expanded by the beam expander 8, incident to the objective lens 14 through the coherency diminishing optical system 15, beam splitter 16, polarizing devices 17, and cast onto the subject (semiconductor wafer) 1. The reflected light from the subject 1 goes up vertically, and is conducted through the objective lens 14, polarizing devices 17, beam splitter 16 and imagery lenses 18 and 19, and detected by the image sensor 20. At the time of inspection, the semiconductor wafer 1, with a pattern being formed thereon, as an example of the subject of inspection is scanned by moving the stage 2, and the focal point detecting system 29 is operated to detect the z-axis position of the inspection surface of the subject 1 continuously and control the z-axis position of the stage 2 so that the distance of the surface from the objective lens 14 is kept constant. The image sensor 20 senses the brightness (tonal image) of the pattern formed on the semiconductor wafer 1 accurately. Resulting information (tonal image signal) is processed by an image processor 50, and the inspection of microscopic defects of the subject 1 is accomplished.

Figure 35:
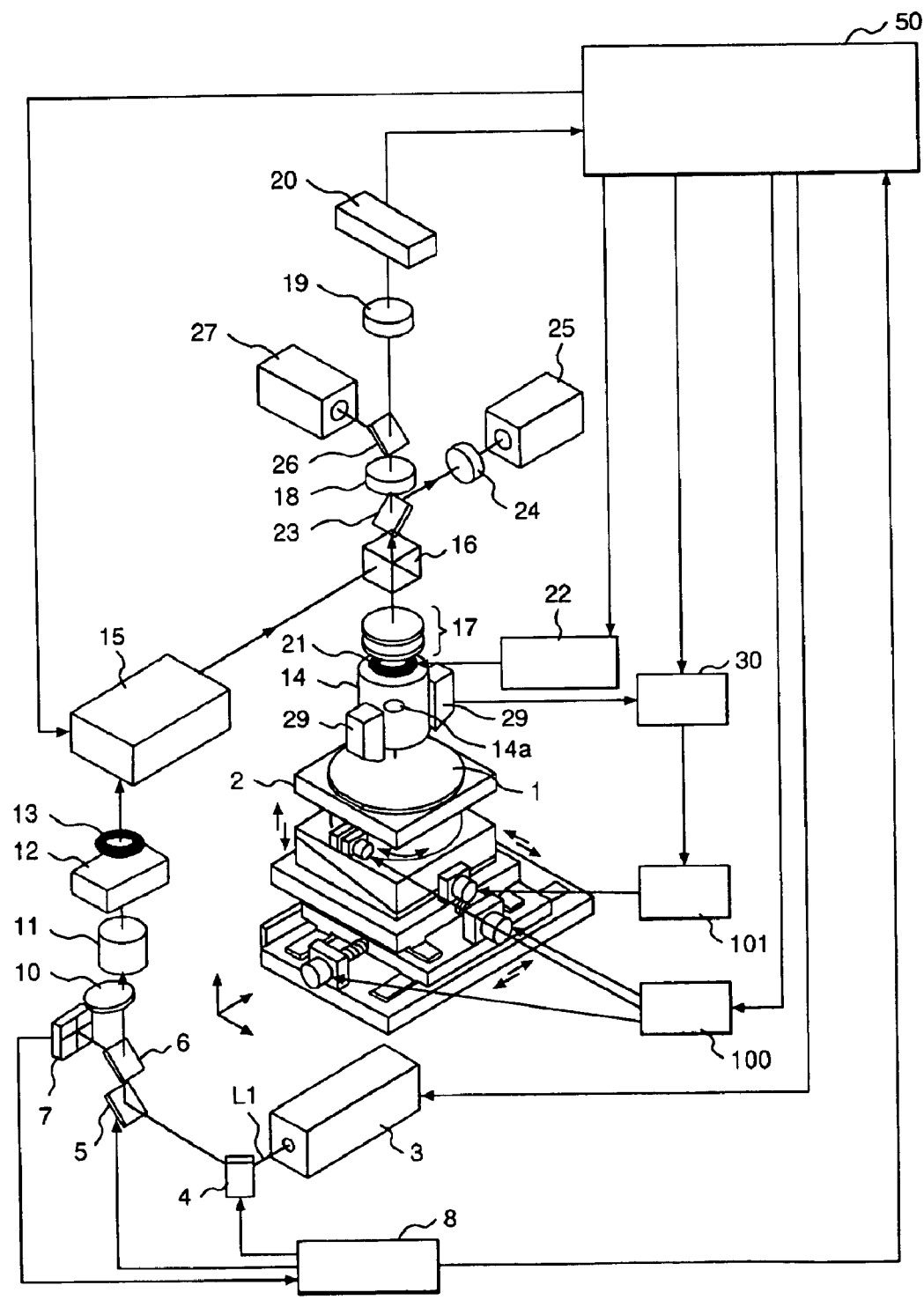
FIG. 35 is a perspective diagram showing in brief the structure of a pattern defect inspection apparatus based on a second embodiment of this invention.

FIG. 35 shows a second embodiment of this invention. This embodiment differs from the foregoing first embodiment in the removal of the imagery lens 19 based on the relocation of the diaphragm 21 from the position before the image sensor 20 to the position immediately before the objective lens. The rest is identical to the first embodiment. Based on the disposition of the diaphragm 21 close to the pupil 14a of the objective lens 14, the same effect as the first embodiment is attained.

Figure 36:
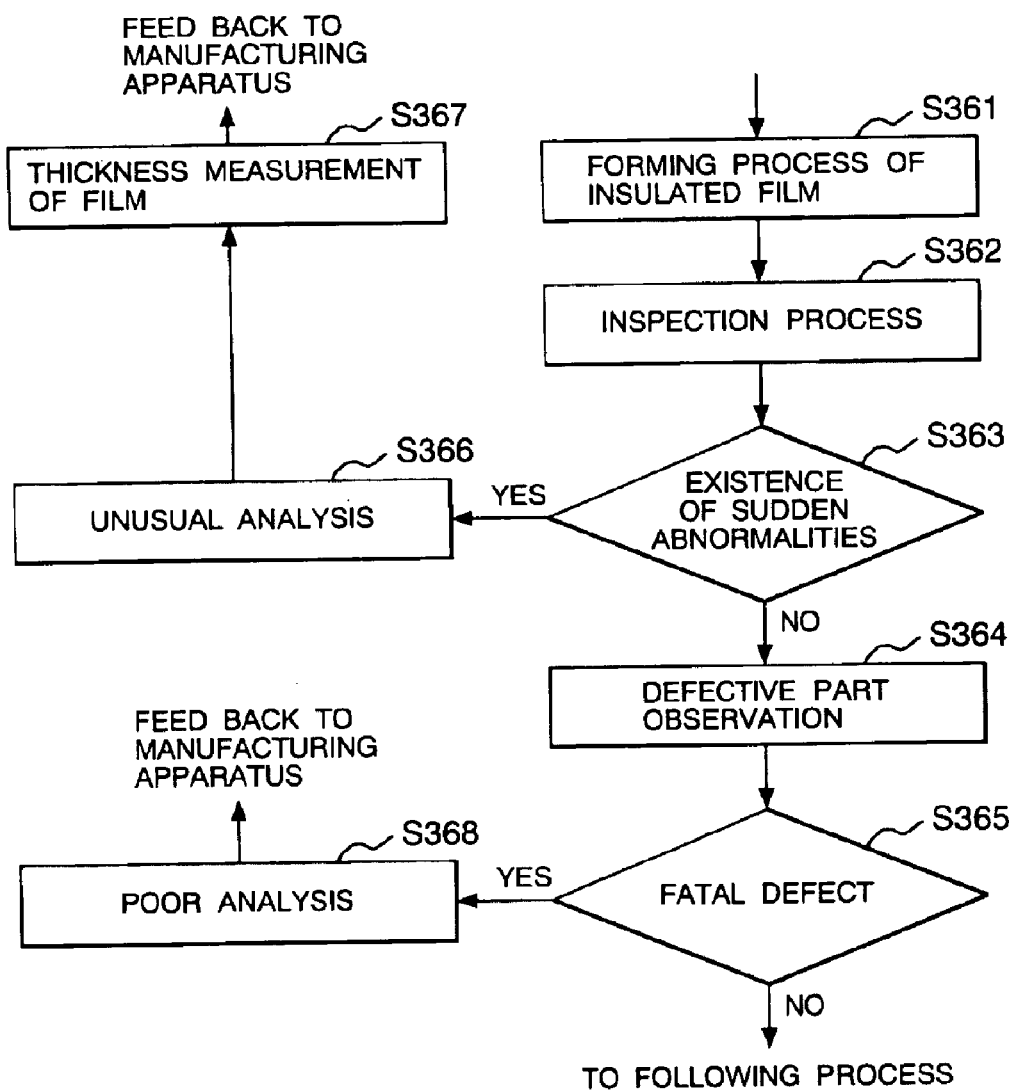
FIG. 36 is a flowchart showing the sequential fabrication process of a semiconductor device based on this invention.

FIG. 36 shows the effective usage of the defect inspection apparatus of the foregoing embodiments for the semiconductor device fabrication process (for example S361). Semiconductor devices such as LSIs are fabricated through a variety of processing steps including steps of laminating transferred patterns. Even if a single line breakage or short-circuit is created in any one step, the following processing will merely result in faulty products. Using this inspection apparatus in inspection process S362, the existence of sudden abnormalities is acquired in process S363 and it becomes possible by analyzing it in process S366 to feed back to for example thickness measurement equipment in process S367. Moreover, if poor analysis is performed and there is no fatal defect by observing the detected defective part in process S364, S365, S368, the rate of the defect will be reduced by letting a process pass as it is. If it is the fatal defect, it will become possible to prevent making a lot of poor products with feeding back to manufacturing apparatus promptly.

As described above, by using the DUV light having a wavelength of 266 nm, 248 nm or 192 nm, inspection of device defects of 0.07 μm rule or smaller can be accomplished. The inventive method and apparatus can be applied for the inspection of Cu damascene as a subject of inspection. Speckles are not created in subject portions where the circuit pattern is absent, and the comparison of a produced image with a reference image does not make a false indication.

The UV light of 365 nm or less in wavelength used for the illumination light has large optical energy, and when optical parts are irradiated by it, organic contaminant decomposes or reacts and sticks on the part surface. By providing the optical parts with an air ventilation means or air blasting means, the deterioration of optical parts can prevented.

Although the bright field optical system has been explained for the embodiments of this invention, the same effectiveness is attained by use of a common focal point microscope for the imaging optical system.

The inventive method and apparatus achieve the high-luminance UV or DUV illumination, enabling the high-resolution imaging in a short time, and as a result a high speed and high sensitivity inspection apparatus is offered. Defects of pattern are detected in terms of their positions and dimensions. Inspection subjects can include damascene of Cu and the like resulting from the buried wiring in contact holes or wiring grooves made by forming a conductive metallic film of Cu or the like and burying in the holes or grooves which are formed on an insulation film of $SiO_2$ or the like, and removing excessive deposited portions by CMP polishing or the like. Accordingly, the inventive inspection method and apparatus can be applied to damascene of Cu or the like.

When the inventive method and apparatus using the DUV light (266 nm, 248 nm or 193 nm in wavelength) are applied to devices of 0.07 μm design rule or smaller, they are very effective in detecting microscopic defects smaller than 0.07 μm.

When the illumination light which is shorter in wavelength than the DUV light is used, the influence of chromatic aberration can be alleviated by use of a reflection objective lens for the objective lens 14.

According to this invention, it is possible based on the illumination of a short wavelength, which is indispensable for the enhancement of resolution, particularly based on a laser light source, which is advantageous for practicing, to produce an image, which is the same or better in quality as compared with the result from the ordinary discharge tube illumination, at the higher sensitivity and higher speed, whereby it is effectively possible to detect microscopic defects at high-sensitivity.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A pattern inspection apparatus for detecting defects comprising:
   a light source which emits ultraviolet (UV) light;
   irradiation means which diminishes a coherency of the UV light and irradiates the UV light having the diminished coherency onto a subject through an objective lens;
   imaging means which images the subject irradiated by the UV light, with the coherency thereof being diminished by said irradiation means, and detects an image signal; and
   defect detecting means which detects a defect of a pattern which is formed on the subject, based on information carried by the image signal detected by said imaging means;
   wherein said irradiation means include a pair of oscillation mirrors, each of the pair of oscillation mirrors being arranged at a position conjugate with a pupil of the objective lens and scanning the UV light emitted from said light source.

2. A pattern inspection apparatus according to claim 1, wherein said UV light emitted by said light source is laser.

3. A pattern inspection apparatus according to claim 2 further including polarization control means which controls state of polarization of the UV laser emitted by said light source.

4. A pattern inspection apparatus according to claim 2 further including coherency diminishing means which diminishes the coherency of the UV laser emitted by said light source.

5. A pattern inspection apparatus according to claim 1, wherein said light quantity adjusting means includes a filter which reduces quantity of light transmitted; and a light quantity setting system which sets arbitrarily the quantity of light transmitted by said filter.

6. A pattern inspection apparatus according to claim 1 further including: optical axis detecting means which detects variation of an optical axis of the UV light emitted by said light source; and optical axis deviation correcting means which corrects deviation of the optical axis detected by said optical axis detecting means.

7. A pattern inspection apparatus according to claim 1 further including diffracted light control means which controls degree of transmission of diffracted light from the subject which is irradiated by the UV light, with coherency thereof being diminished by said irradiation means.

8. A pattern inspection apparatus according to claim 1, wherein said defect detecting means includes: a memory which stores a reference image signal; a brightness corrector which corrects brightness level of at least one of the detected image signal detected by said imaging means and the reference image signal stored in said memory so that brightness level of a normal portion of the detected image signal is virtually equal to brightness level of a normal portion of the reference image signal; and a defect detector which compares the image signal corrected by said brightness corrector with the other image signal thereby to detect a defect of the pattern formed on the subject.

9. A pattern inspection apparatus according to claim 3, wherein said polarization control means includes one or both of a quarterwave plate or a halfwave plate and quarterwave plate disposed on the light path ranging from said UV light source up to the subject, and an analyzer disposed on the light path of the light reflected by the subject ranging from the subject up to the detector of said image detecting means.

10. A pattern inspection apparatus according to claim 1, wherein said imaging means includes an image sensor of the time delay integration type having the anti-blooming characteristics.

11. A pattern inspection apparatus according to claim 1, wherein said imaging means includes an image sensor of the time delay integration of rear-surface irradiation type.

12. A pattern inspection apparatus for defect detection comprising:
a light source which emits UV light;
irradiation means which diminishes coherency of the UV light emitted from said light source by scanning the UV light on a pupil of an objective lens by a pair of swinging mirrors, controls a polarization state of the UV light, and irradiates the UV light having the coherency diminished and the polarization state controlled onto a subject through said objective lens;
imaging means which images the subject being irradiated with the UV light by said irradiation means; and
defect detecting means which processes the image of subject detected by said imaging means thereby to detect a defect,
wherein said defect detecting means detects a defect of the order of 100 nm in size of a pattern formed on a subject wafer while processing wafers of 200 mm in diameter at a processing speed of 3 wafers per hour or higher.

13. A pattern inspection apparatus according to claim 12, wherein said irradiation means includes: a diffusion plate disposed near a position conjugate with the subject; means of rotating said diffusion plate; an objective lens; and a swing mirror which is disposed at a position conjugate with a pupil of said objective lens, wherein said swing mirror deflects the UV light to scan at the position conjugate with the pupil of said objective lens.

14. A pattern inspection apparatus according to claim 12, wherein said irradiation means includes an objective lens having an NA value of 0.75 or larger and irradiating the UV light onto the subject through said objective lens.

15. A pattern inspection method for defect detection comprising the steps of:
irradiating UV light having diminished coherency onto a subject, with a pattern being formed thereon, through an objective lens;
imaging the subject, which is irradiated by the resulting UV light, through said objective lens to detect an image signal;
correcting brightness level of at least one of the detected image signal and a reference image signal so that brightness level of a normal portion of the detected image signal is virtually equal to brightness level of a normal portion of the reference image signal; and
comparing the corrected image signal with the other image signal to detect a defect of the pattern.

16. A pattern inspection method according to claim 15, wherein the step of irradiating the resulting UV light includes the step of diminishing coherency thereof by scanning the UV light being converged on a pupil of said objective lens.

17. A pattern inspection method according to claim 15, wherein the step of irradiating the resulting UV light includes the step of controlling polarization state of the UV light.

18. A pattern inspection method according to claim 15, wherein the step of imaging the subject includes the step of controlling polarization state to detect the image signal.

19. A pattern inspection method for defect detection comprising the steps of:
diminishing coherency of a laser which is emitted by a laser light source;
irradiating the laser, with coherency thereof being diminished, through an objective lens onto a subject with a pattern being formed thereon, while varying irradiation direction of the laser through the objective lens with time;
imaging the irradiated subject to obtain an image signal; and
comparing the obtained image signal with a reference image signal to detect a defect of the pattern;
wherein the step of irradiating includes scanning the laser on a pupil of the objective lens by scanning with a pair of galvanomirors.

20. A pattern inspection method according to claim 19, wherein the step of imaging includes the step of controlling polarization state to obtain the image signal.

21. A pattern inspection method for a pattern formed on a subject, said method comprising the steps of:
irradiating UV laser, which coherency is diminished by scanning the UV laser with a pair of galvanomirrors, onto a surface of the subject;
imaging the surface of the subject which is irradiated by the UV laser, to obtain an image signal;
processing the obtained image signal to detect a defect of 100 nm or less in size on the subject; and
releasing information in relation to position of a detected defect of 100 nm or less in size on the subject.

22. A pattern inspection method according to claim 21, wherein the step of imaging the surface of the subject includes the step of controlling polarization state at the time of imaging.

23. A pattern inspection method according to claim 21, wherein the UV laser has a wavelength between 50 nm and 400 nm.

* * * * *